United States Patent
Kirschenbaum

(10) Patent No.: US 8,188,453 B2
(45) Date of Patent: May 29, 2012

(54) SHORT USE SYSTEM AND METHOD FOR ADAPTIVE RADIATION PROTECTION

(76) Inventor: Ira Kirschenbaum, Scarsdale, NY (US)

( * ) Notice: Subject to any disclaimer, the term of this patent is extended or adjusted under 35 U.S.C. 154(b) by 52 days.

(21) Appl. No.: 12/377,466

(22) PCT Filed: Oct. 11, 2007

(86) PCT No.: PCT/US2007/081163
§ 371 (c)(1),
(2), (4) Date: Mar. 15, 2010

(87) PCT Pub. No.: WO2008/097382
PCT Pub. Date: Aug. 14, 2008

(65) Prior Publication Data
US 2010/0163758 A1    Jul. 1, 2010

Related U.S. Application Data

(60) Provisional application No. 60/828,977, filed on Oct. 11, 2006.

(51) Int. Cl.
*G21F 3/02* (2006.01)
(52) U.S. Cl. .................................................. 250/516.1
(58) Field of Classification Search ............... 250/515.1, 250/516.1
See application file for complete search history.

(56) References Cited

U.S. PATENT DOCUMENTS

| | | | | |
|---|---|---|---|---|
| 3,310,053 A * | 3/1967 | Greenwood | ................ | 450/153 |
| 4,164,217 A | 8/1979 | Schrock | | |
| 4,197,947 A | 4/1980 | Zaidi | | |
| 4,415,089 A * | 11/1983 | Ruffa | ................ | 211/85.13 |
| 4,938,233 A * | 7/1990 | Orrison, Jr. | ................ | 128/849 |
| 4,938,633 A * | 7/1990 | Wu et al. | ................ | 405/229 |
| 5,015,865 A * | 5/1991 | Sayers | ................ | 250/516.1 |
| 5,045,708 A * | 9/1991 | Cooper | ................ | 250/519.1 |
| 5,054,127 A | 10/1991 | Zevchak | | |
| 5,103,504 A * | 4/1992 | Dordevic | ................ | 2/243.1 |
| 5,105,473 A | 4/1992 | Valtakari | | |
| 5,115,140 A * | 5/1992 | Rodriguez | ................ | 250/516.1 |
| 5,247,182 A * | 9/1993 | Servant et al. | ................ | 250/516.1 |
| 5,346,297 A | 9/1994 | Colson, Jr. et al. | | |
| 5,453,314 A * | 9/1995 | Collier et al. | ................ | 428/198 |
| 5,497,511 A * | 3/1996 | Zade | ................ | 2/22 |
| 5,621,188 A * | 4/1997 | Lee et al. | ................ | 174/390 |
| 5,638,545 A * | 6/1997 | Rosner | ................ | 2/16 |
| 6,233,740 B1 * | 5/2001 | Meyers et al. | ................ | 2/102 |

(Continued)

OTHER PUBLICATIONS

PCT/US07/81163 filed Oct. 11, 2007, International Search Report and Written Opinion mailed Sep. 10, 2008, 11 pages.

*Primary Examiner* — Jack Berman
*Assistant Examiner* — Jason McCormack
(74) *Attorney, Agent, or Firm* — Kilpatrick Townsend & Stockton LLP

(57) ABSTRACT

A short use or disposable system and method for adaptive window-capable radiation protection provides a disposable outer covering for securing one or more flexible and overlappable radiation shield members relative to a user using a variety of features including pockets, pocket defining members, fitting aid members, and fixing and releasing points. Features allow conveniently securing multiple layers of reusable shields in disposable coverings and providing pre-selected and assembled shielding kits for specific uses. Variants provide adaptive shielding sheets that may be customized to a particular patient need or injury profile.

14 Claims, 17 Drawing Sheets

U.S. PATENT DOCUMENTS

| | | |
|---|---|---|
| 6,289,524 B1 | 9/2001 | Wright et al. |
| 6,332,712 B1 * | 12/2001 | Headley .......................... 383/64 |
| 2004/0156755 A1 * | 8/2004 | Wardlaw ....................... 422/102 |
| 2004/0199983 A1 | 10/2004 | Gillen et al. |
| 2005/0211930 A1 * | 9/2005 | DeMeo et al. .............. 250/516.1 |
| 2006/0108548 A1 | 5/2006 | Cadwalader et al. |
| 2008/0189832 A1 * | 8/2008 | Oscher .............................. 2/400 |
| 2008/0295210 A1 * | 12/2008 | Matic et al. ........................ 2/2.5 |

\* cited by examiner

SHORT USE SYSTEM AND METHOD FOR ADAPTIVE RADIATION PROTECTION

CROSS REFERENCE TO RELATED APPLICATIONS

This application claims priority from PCT Application Serial No. PCT/US07/81163 filed Oct. 11, 2007 and U.S. Provisional Application Ser. No. 60/828,977, filed Oct. 11, 2006, the contents of each of which are incorporated by reference.

FIGURE SELECTED FOR PUBLICATION

FIG. 1A

BACKGROUND OF THE INVENTION

1. Field of the Invention

The present invention relates to a short use or disposable protective system for ready use for adaptive medical x-ray imaging. More specifically, the present invention relates to a system and method for enabling short use readily adapted pouch-based garments with removable and reusable shielding to enable various imagery positions in a window-capable format.

2. Description of the Related Art

Referring now to FIG. 1, the related art involves a multi-player lead-containing sheet 105 that is draped over a user's body during X-ray radiation imagery to restrict the passage of X-rays (or other high-energy electromagnetic waves) to unintended portions of the body.

Sheets 105 contain an outer nylon layer on each side 102, 202 bounding one or more flexible lead-containing thin sheets 100, and bound at a perimetral location by a binding 103. Nylon outer layers 102, 102 are commonly woven and impregnated with a water-proof or fluid-resistant coating so that when sheets 105 are washed between uses, the water or sterilizing fluid employed does not penetrate the multi-layer lead sheet construction and build-up there within to the detriment of the assembly.

The thin sheets 100 of lead and the use of multiple layers allows sheet 105 to be somewhat flexible and they can slide slightly relative to each other, allowing some relative movement between sheets despite the edge binding 103, but overall the item itself is heavy and awkward to use and difficult to position, particularly in larger sizes, in emergency-treatment-type situations, or during transportation circumstances, and generally wherever an individual is injured and unable to be conveniently covered.

This type of construction provides several detriments to user safety, including the relative inflexibility that leads to coverage gaps in the X-ray protection, and difficulty in cleaning between uses that may result in biological contamination or transfer between users.

A similar detriment to the present constructions is the difficulty in positioning the conventional shield 105 on children or adults with non-standard body types or physical disabilities (deformities, sever injuries, obesity, immobility, pregnancy, tiny-size (infants) etc.). This form of detriment is even more critical when using X-rays to image a patient's most radiation sensitive regions close to or including a spine, skull, chest, hips, thyroid, glands, brain, organs, eyes or other regions that contain X-ray sensitive soft-tissue items.

In a related note, one of the difficulties in properly shielding patients from high energy imaging X-rays is the backscatter or bounce-back effect. This effect is best understood with the following example. A patient is positioned on a metal support surface (a conventional X-ray imaging table), and a heavy conventional shield is draped over (for example) their chest region. The imagery goal in this example is to produce an X-ray image of a left hip joint so that the conventional shield crosses the patient's pelvis at an angle to the spine exposing the left hip joint and just covering the right hip joint and one hopes the user's radiation-sensitive reproductive organs. The film is positioned below the user's pelvis at an angle.

Upon the delivery of X-ray energy to the left hip joint region, the film is exposed but the patient actually receives a greater dose of X-ray energy then the film since a portion of the energy is either blocked by the patient's flesh and bone, reflected from the support surface back into the soft tissue (a "double-hit") causing additional harm and what will be referred to as low-dose X-ray exposure even in the regions visually blocked by the conventional shielding.

As an additional detriment, this form of low-dose X-ray exposure may be of little importance in one-time exposure for an adult past child bearing years but may have a material and detrimental impact upon a growing child, a pregnant women, or a adult of reproductive years; particularly where that user requires repeated exposure—for example during multiple corrective spinal treatments, during cancer treatments, or during treatment for a skeletal deformity. In sum, the medical profession has not appreciated the need to both compartmentalize and to minimize this low-dose exposure and has yet provide a flexible system that will work for all patients and is adaptable to surgical and medical requirements.

In a similar concern, certain forms of X-ray or other electromagnetic-wave imagery may require higher-than-normal levels of exposure for a patient in order to generate film clarity. This type of situation is often required where a patient has received facial injury or soft-tissue injury and a higher radiation dosage is required to illuminate the soft-tissue differences. In such circumstances, a physician may require a higher form of radiation that requires a corresponding increase in patient protection.

Similarly, as introduced above, emergency medical care is seldom neat and clean for all its life-saving result. This is particularly true in high-volume hospital emergency room environments or in, military treatment or battle-close environments where rapid diagnosis is critical, wounds are massive, bodily fluids are on all surfaces, and treatment professionals are repeatedly exposed. In these types of high-activity environments, X-ray imagery is often provided with minimalist efforts of protection (to either the patient or the staff for good medical reasons or needs involving swiftness of diagnosis) and priority is given to diagnosis not ultimately cleanliness (also for good medical reasons). Unfortunately, both situations often result in the re-use of biologically contaminated conventional shields and undue-amounts of damaging radiation.

Some single-use protective shields have been suggested in the art. For example, Servant (U.S. Pat. No. 5,247,182) provides a belt-on shield to protect a user from diverse-in-line radiation. As disclosed, the belt-on shield is a layer effective to attenuate energy to the gonadal region of a user (disclosed as an X-ray operation technician). Servant responds solely to the needs of a user receiving direct radiation from a front-wise direction and obviously fails to recognize the need to protect the testis of a male user from non-direct radiation or either hip-joint and the soft tissue therein. Similarly, Servant fails to supply any form of protective and disposable cover, or the need to secure the shield to the patient other than by gravity via the belt support.

Also illustrative of the earlier failures in the art is Greenwood (U.S. Pat. No. 3,310,053) that includes a form of elastomeric girdle worn by female X-ray technicians and including a pocket for receiving a flat rigid plate member so that users may continually operate in a somewhat protective manner throughout the work cycle so as to minimize unintended X-ray (or gamma-ray) radiation exposure.

What is not appreciated by the prior art is the need for a disposable shield cover to minimize biological contamination between patients and to enhance flexibility of use. The related art also fails to appreciate the need for a pre-packaged kit containing specific shielding items responsive to a particular medical need, wherein such a kit may be prepared and transported in a clean and a pre-packaged manner to minimize contamination. Also related is the need for a disposable and protective supporting garment that may readily accept previously-used radiative shielding and position it effectively to both shield a patient and prevent biological contamination between prior, present, and future users.

What is also not appreciated by the prior art is the need for a shielding system that is readily customizable to emergency or military-type care or to greatly differing body styles.

The related art has also failed to appreciate the detrimental impact of high-energy scattered radiation on patients and the need for shielding that is responsive to particularized imaging scenarios; for example shields specific to a bikini/brief need, an ovary/uterine need, a ½ chest need, a thyroid protection need, a particular spine or head protective need, a minor child protective need, and those who are obese or who are unable to assume common imagery body positions as a result of injury or physical detriment or deformity.

The related art similarly fails to appreciate the benefit of shield layering for increased movement or the need to protect patients from back-scattered or reflected radiation off a patient support surface.

Accordingly, there is a need for an improved disposable system and method for adaptive radiation protection that appreciates at least one of the challenges noted above.

ASPECTS AND SUMMARY OF THE INVENTION

An aspect of the present invention is to provide a disposable system and method for adaptive radiation protection that responds to at least one of the needs noted above.

Another aspect of the present invention is to provide an adaptive shielding system that may be readily distributed in a kit form with variable layers of shielding protection (for example, a base layer for common use, and an additional layer where higher dose radiation is needed required for imagery).

Another aspect of the present system is to provide a garment that is easily fitted and modified to non-standard users, such as children, the disabled, or obese.

Another aspect of the present invention is to provide a garment comprising a disposable sheet material having at least one system for coupling a shielding protection member to the sheet material.

The present invention relates to a window-capable disposable system and method for adaptive radiation protection that provides a disposable outer covering for securing one or more inner-relatable or overlapping flexible radiation shield members. Features allow conveniently securing multiple layers of shields and providing pre-selected shielding kits for specific uses. Variants provide adaptive shielding sheets that may be customized to a particular patient need.

According to an embodiment of the present invention there is provided a protective shielding garment for protecting a user receiving high energy radiation, comprising: a disposable member layer, means for positioning the disposable member layer in a user protective position prior to receiving the high energy radiation, and at least one bounding pocket in the member layer for receiving a first shielding member there within.

According to another optional embodiment of the present invention there is provided a protective shielding garment further comprising: means for securing an additional adaptive shielding member to an external region of the disposable member layer, whereby a shielding capacity of the garment may be increased a medically-desirable amount.

According to another optional embodiment of the present invention there is provided a shielding system, comprising: a first pocket member constructed from a short use material, and at least a first radiation shielding member removably positionable in the first pocket member, whereby the shielding system enables selective disposal of the first pocket member after use while protecting the shielding member for later reuse.

According to another optional embodiment of the present invention there is provided a protective shielding station, comprising: a defined region for storing a plurality of kit members, each the kit member further comprising: means for securely containing a protective shielding garment system in a sterile environment prior to an opening of the kit member, each the protective shielding garment system, further comprising: a disposable member layer, means for positioning the disposable member layer in a user protective position prior to receiving the high energy radiation, at least one bounding pocket in the member layer for receiving a first shielding member there within, and means for securing an additional adaptive shielding member to an external region of the disposable member layer.

According to another optional embodiment of the present invention there is provided a shielding system, comprising: a sheet good containing a plurality of spaced securing regions on a surface thereof, the sheet good including a plurality of separation regions defined between respective the plurality of spaced securing regions, a plurality of individual shielding elements shaped for reception at the spaced securing regions, and at least one of the separation regions including a removal force reduction means for easing a separation of a first portion of the sheet good from a remainder portion of the sheet good, whereby the shielding system is readily adaptable to a variety of shapes.

According to another optional embodiment of the present invention there is provided a shielding system, wherein: the sheet good is one of a disposable and a non-disposable sheet good.

The above, and other aspects, features and advantages of the present invention will become apparent from the following description read in conduction with the accompanying drawings, in which like reference numerals designate the same elements.

BRIEF DESCRIPTION OF THE DRAWINGS

FIG. 2D is a perspective view of a shielding bikini brief and a first additional adaptive shielding element that supports a second additional adaptive shielding element extending there from.

DETAILED DESCRIPTION OF THE PREFERRED EMBODIMENTS

Figures 1, 1A:
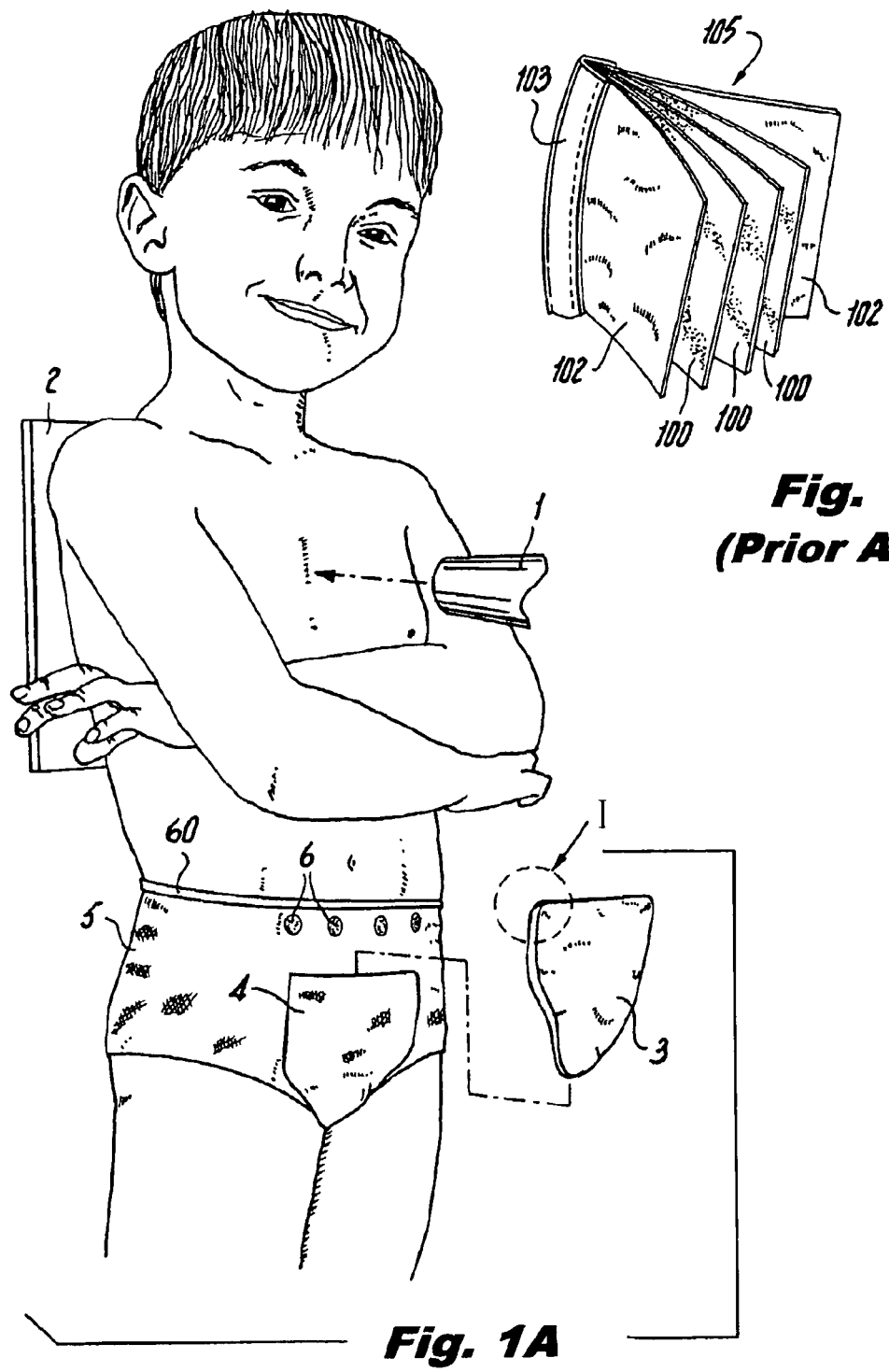
FIG. 1 is a sectional view of a conventional multi-layer lead shield.
FIG. 1A is a perspective view of one embodiment of the present invention shown as a boys brief garment assembly.

Reference will now be made in detail to several embodiments of the invention that are illustrated in the accompanying drawings. Wherever possible, same or similar reference numerals are used in the drawings and the description to refer to the same or like parts or steps. The drawings are in simplified form and are not to precise scale. For purposes of convenience and clarity only, directional terms, such as top, bottom, up, down, over, above, and below may be used with respect to the drawings. These and similar directional terms should not be construed to limit the scope of the invention in any manner. The words "connect," "couple," and similar terms with their inflectional morphemes do not necessarily denote direct and immediate connections, but also include connections through mediate elements or devices.

Referring now to FIG. 1A a short use brief system includes a brief body 5 constructed from a single-or-low-use-capable disposable material such as non-woven and non-absorptive Tyvek®-type material having an elastic waist band member 60 or strap operating as a fitting aid member, and a plurality of attachment regions 6, to enable windowing as will be discussed. A pocket defining member 4 is constructed over a genital region of the user and extends downwardly from a location approximate the hip level to between the user's legs so as to slidably receive a flexible and removable shield member 4.

As discussed elsewhere, here the user is a young boy interposed between an X-ray or radiation source 1 and an imaging target 2. In this image it is proposed that the short-use or disposable briefs 5 are more readily worn by children due to the size difference, their similarity to existing children's underwear, and the generally uncooperative nature of children to remain quiet during imaging.

Figure 1B:
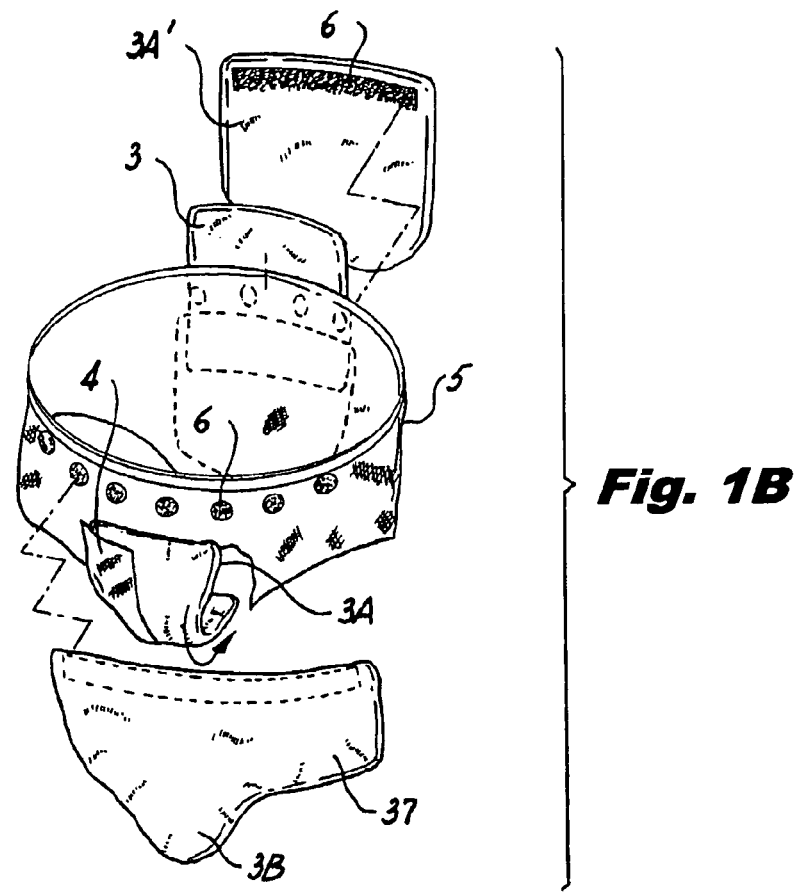
FIG. 1B is an exploded perspective view of the boys brief garment shown in FIG. 1A with additional shielding elements.

Referring now to FIG. 1B, brief assembly 5 having pocket 6 and attachment locations 6 now slidably receives a securely releaseable three dimensional shield member 3A which is shaped and sufficiently flexible to enclose the user's genitals. The present depiction notes the use of a rear-pocket (shown in shadow) receiving a flexible rear shielding member 3 (like the front shield in FIG. 1A) to minimize the impact of reflected radiation through a user's body. This embodiment notes the inclusion of a second layer of adaptive shielding members 3A' and 3B having joining members 6 for attaching to corresponding attachment points 6 on adaptive shielding members.

As noted, adaptive shielding member 3B includes a wide side-hip-extension 37 that readily extends to cover and protects a child's hip joint while allowing imagery freedom of the opposite hip joint. As a consequence, a windowing-ability relative to an imagery of, for example a hip joint, reduces a patient's exposure to both direct radiation, and reflected radiation via rear shield 3A'.

Figure 1C:
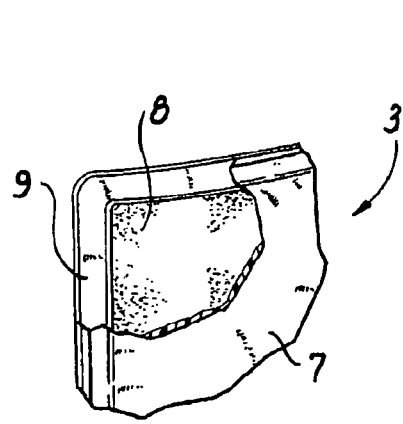
FIG. 1C is a close-up view of section I in FIG. 1A showing a partially cut-away view of one of the shielding elements in the present invention.
Figure 1D:
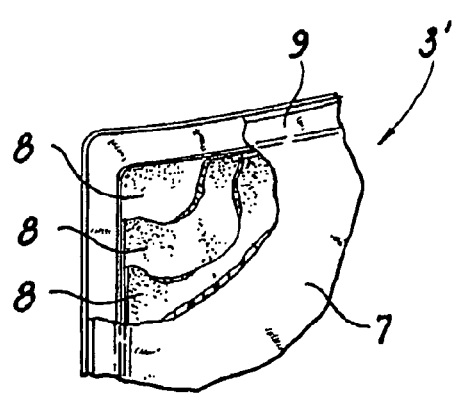
FIG. 1D is a close-up view of section I in FIG. 1A showing a partially cut away view of one of the multi-layer shielding elements of the present invention.

Referring now to FIGS. 1C and 1D, alternative flexible shielding members 3, 3A' are disclosed with cut-away portions I from FIG. 1A. In each circumstance a polymeric coating 7 is provided for complete water-proof protection of inner shielding layers 8, and is sealed proximate an outer edge along a heat-seam 9. One aspect of the present invention is noted in these two figures; namely, the use of flexible layering of shielding. For example, a very flexible single sheet shield 3 may be slipped with pocket 4 to provide better protection then without protection at all where a child rejects the use of a bulky monolithic shield.

Where the X-ray imagery is close to the user's briefs an additional layer of a less flexible shield 3' is included via the plurality of attachment points 6, 6 or Velcro sheeting.

As noted below, one particular improvement over the related art is the generation of sealed shields that are fully capable of rapid sterilization with washing, the use of high temperature autoclave, or other means previously lacking within the art. Similarly, while the present system is not limited by shield size, it is recognized that generally smaller sized shields may be more readily cleaned and sterilized. In contrast, many of the conventional shields are simply too large and unwieldy to readily clean. Additionally, while the present system does not require sealed shields, and may be employed with conventional shielding materials reduced in size, such a use fails to achieve the optimal conditions available.

As similarly noted below, the present embodiment is shown with disposable or single-use briefs constructed from a non-absorptive Tyvek-like or nylon material or other non-fluid absorptive material that may be removed in a sterile condition from a prepared ready-pack and combined with a previously used shield and directly contact the user's private regions without worry of cross-user-contamination, loss of bladder-bowel control, or bleeding injury, as both the user's skin and the previously used shield are maintained separately.

Figures 1E, 1F:
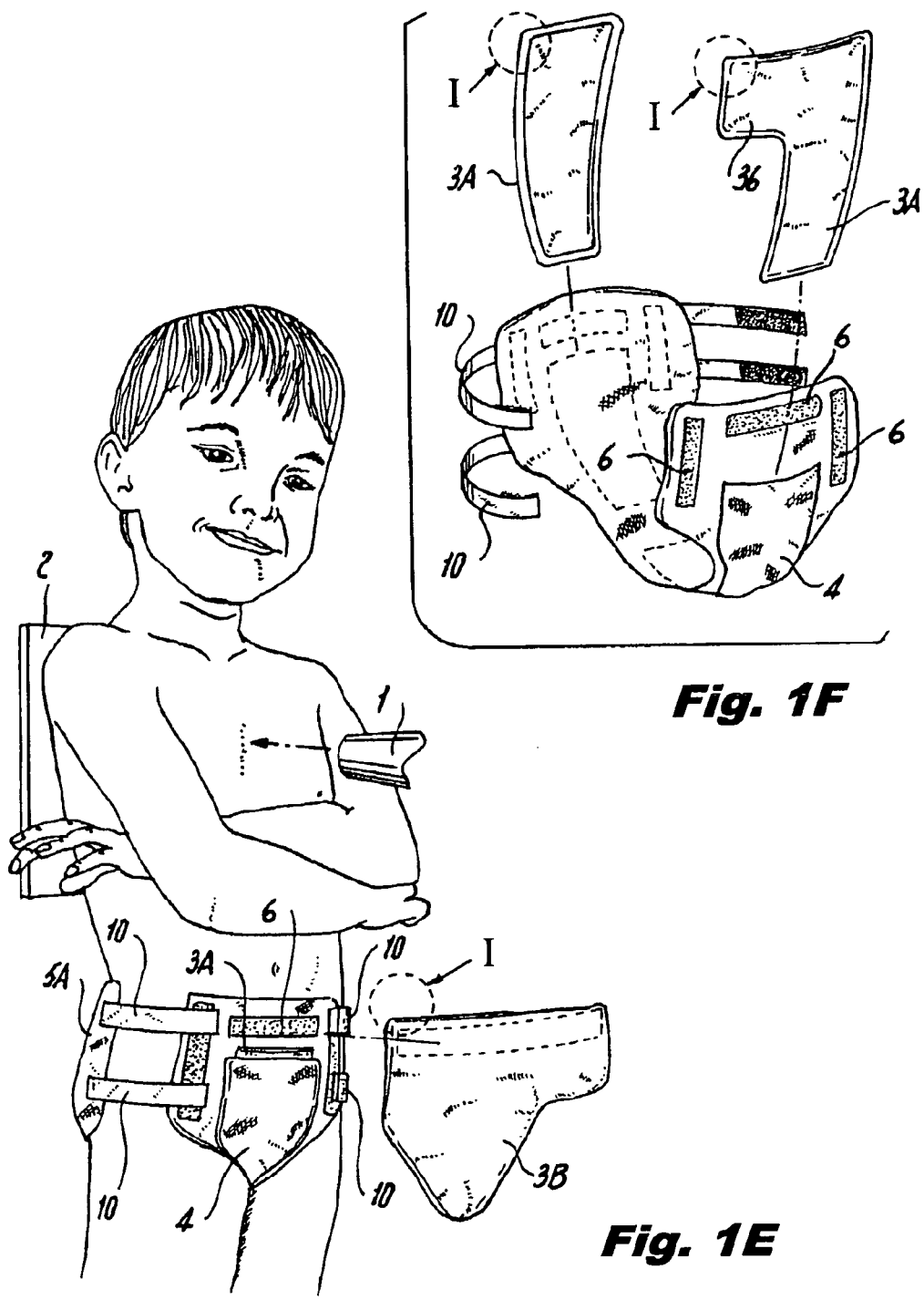
FIG. 1E is a perspective view of another embodiment of the present invention shown as a shielding brief garment with ready adjustment features.
FIG. 1F is an exploded view of the shielding brief garment noted in FIG. 1E.

Referring now to FIGS. 1E and 1F, an alternative brief assembly 5A is provided on a user. In this construction, brief assembly 5A is formed as a diaper and may be similarly combined with absorptive padding for use with incontinent patients or those patients with rectal bleeding or vaginal discharge, sexually transmitted diseases, etc. Front and rear receiving pockets 4, 4 serves as a means for positioning first level shielding 3A, as shown. Brief assembly 5A is similarly constructed in the manner noted above, but here may be easily positioned on a patient who cannot otherwise pull briefs or bikini's over their legs. Side straps 10, 10 joint fixing points 6 on the sides to secure assembly 5A. It is noted, that front first layer 3A as shown is provided with a hip extension member 36 that projects out of front pocket 4 to cover a patient's right hip. As is also provided a secondary shielding layer 3B includes an inner surface Velcro member and joins brief assembly 5A at fixing points 6 on the front portion, as shown.

In this manner, those of skill in the art will recognize that both inner or first layer shields 3A may be adapted in differing shapes as well as outer layers 3B so as to allow a physical or trained user to tailor the shielding system to the degree of radiation protection and geometry required.

As an additional feature, it is readily noted that rear first layer 3A is formed in a differing geometry from front first layer 3A so as to adapt to the pocket construction of strap on brief 5A.

Figures 1G, 1H:
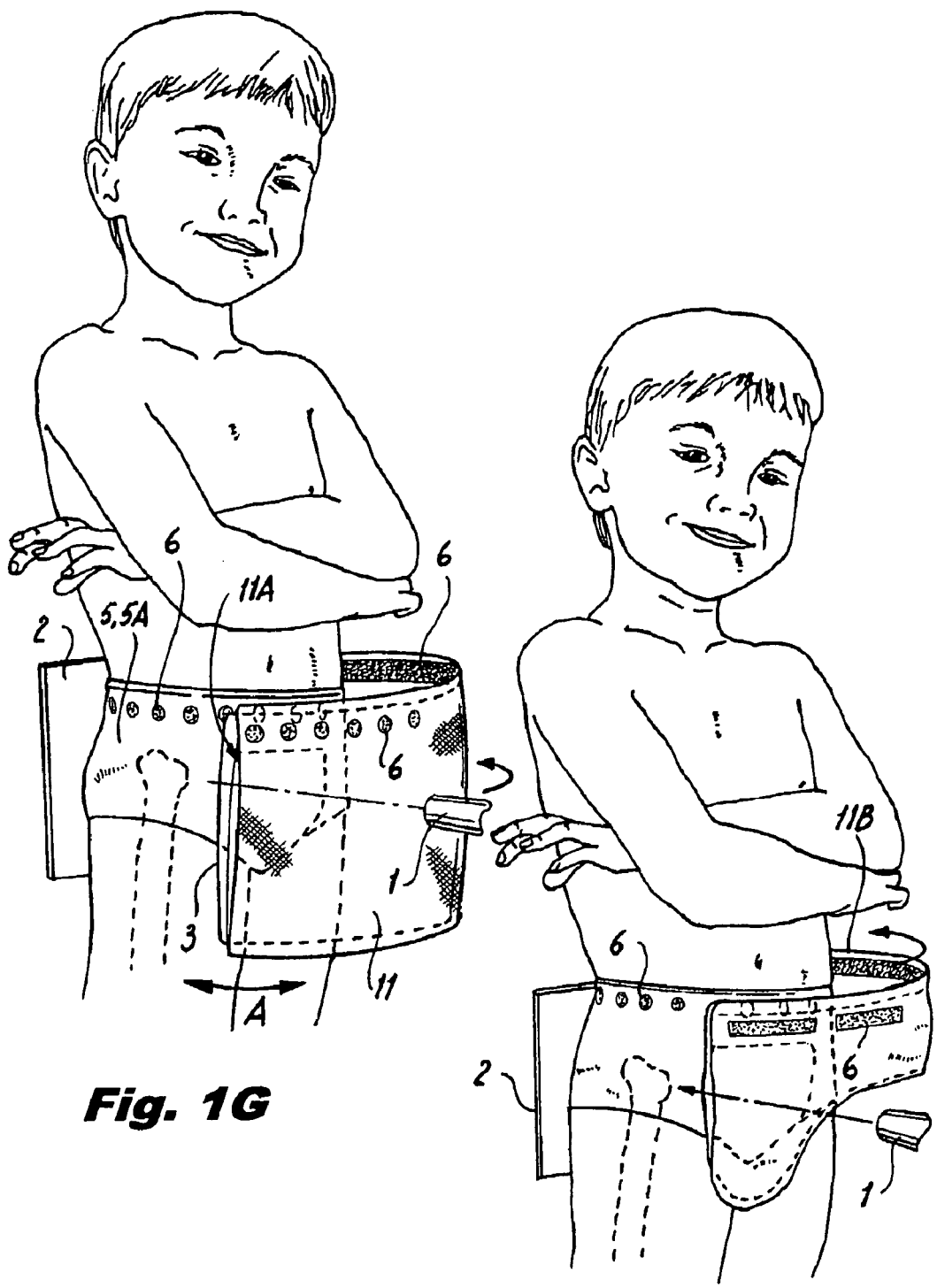
FIG. 1G is a perspective view of an adaptive shielding element repositionably fixable to a shielding brief garment to provide additional protection.
FIG. 1H is a variant of the adaptive shielding element noted in FIG. 1G.

Referring now to FIGS. 1G and 1H, a user is shown wearing either type of brief system 5, 5A with inner layer shieldings 3A in place as a precursor situation. As shown the patient is prepared for imaging a right side hip joint and so requires additional layers or shielding to protect the left side hip joint or lower abdomen. As a result, adaptive secondary shielding members formed as shielding wraps 11, 11B are fixed to brief system 5, 5A via attachment points 6 using motion A into an adjustment position with an edge along a user's torso allowing imagery of only the hip joint. This is a form of windowing the image region in the patient while minimizing exposure of adjacent sensitive regions. As is noted in FIGS. 1G and 1H, pocket-based or pocketed shielding wraps 11, 11B may assume adaptive shapes suited to a medically required geometry and may be removably or permanently affixed to either reach other or to an underlying disposable support garment without departing from the spirit and scope of the present invention.

Figure 1I:
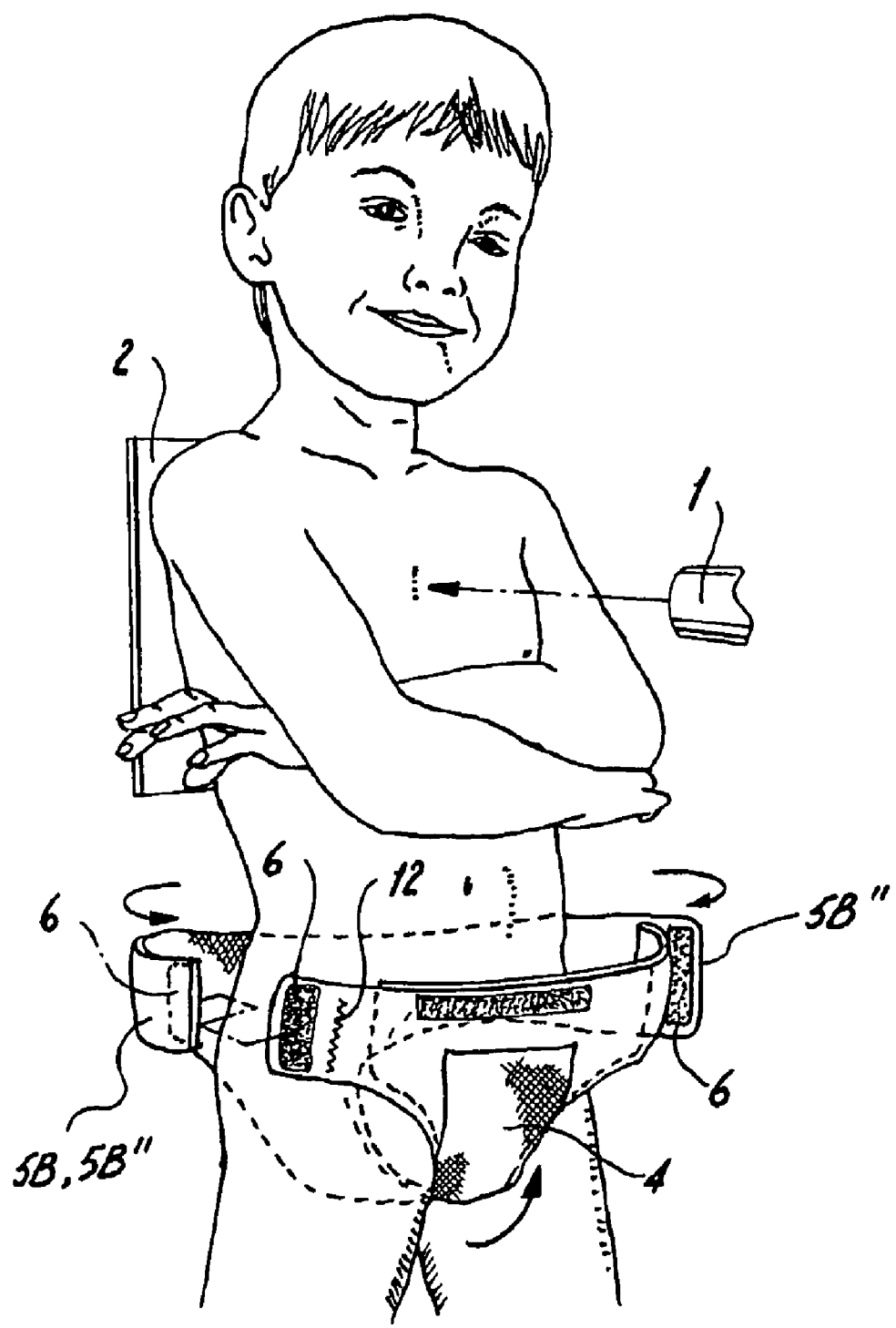
FIG. 1I is a perspective view of another adaptive shielding brief with adjustment features.

Referring now to FIG. 1I, an alternative a brief or bikini form 5B is provided in a manner similar to FIG. 1F, wherein here pocket 4 extends continuously through a users legs front-to-rear and will accept receipt of a flexible and formed first layer shield 3B. What is noted here, is that during adjustment to the patient via side straps and Velcro® portions, an elastic or expansive joint 12 is provided on either strap, and that multiple additional attachment points are established for affixing additional pocketed shielding members.

During assembly, particularly with small children comfortable with the present diapers known to those of skill in the art, a user may simply pull side straps into position and allow elastic joint 12 to retain system 5B in secure position during use. The use of such a diaper shaped embodiment is particularly suited to injured patients who are very young or inconstant.

Figure 2A:
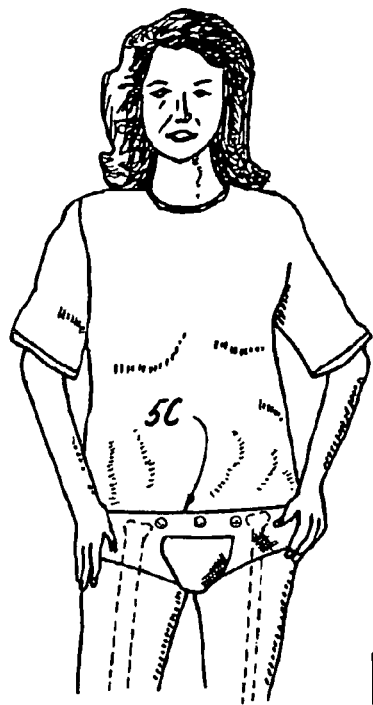
FIG. 2A is a perspective view of shielding bikini according to another embodiment of the present invention.
Figure 2B:
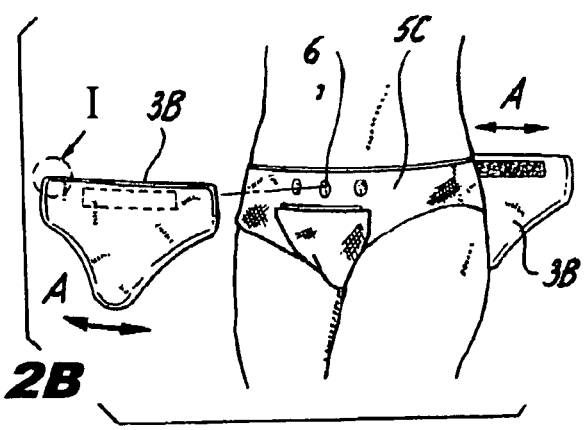
FIG. 2B is a close up perspective view of the shielding bikini shown in FIG. 2A with the inclusion of additional adaptive shielding elements.
Figure 2C:
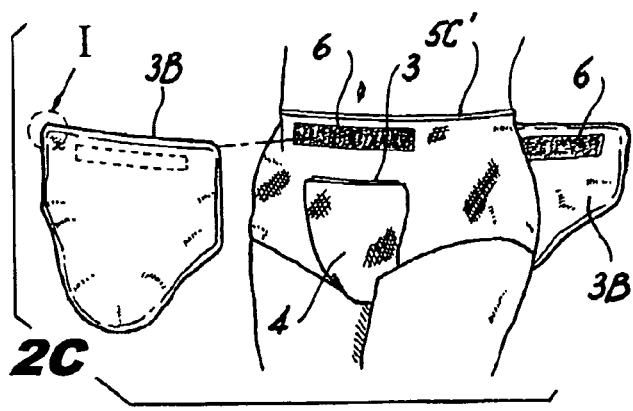
FIG. 2C is an alternative form of a shielding bikini noted in FIG. 2A with additional adaptive shielding elements.

Referring now to FIGS. 2A, 2B, and 2C, a bikini type system 5C and 5C' is proposed for mature female users, or those who are disabled, so as to cover a female user's ovaries and reproductive organs in a convenient manner. As noted before with brief constructions 5 (FIG. 1A), 5A (FIG. 1E), bikini system 5C and 5C' are differently formed from short-use type materials and include front and rear pockets 4 for receiving flexible inner shields 3. A plurality of external attachment or connection portions 6 allow attachment of and removably engage secondary layer shields 3B, 3B via motions A, A so as to provide an enhanced shielding effect. As is noted above, both shields 3 and 3B may be adaptively shaped to protect one or both adjacent hip joints.

Figure 2D:
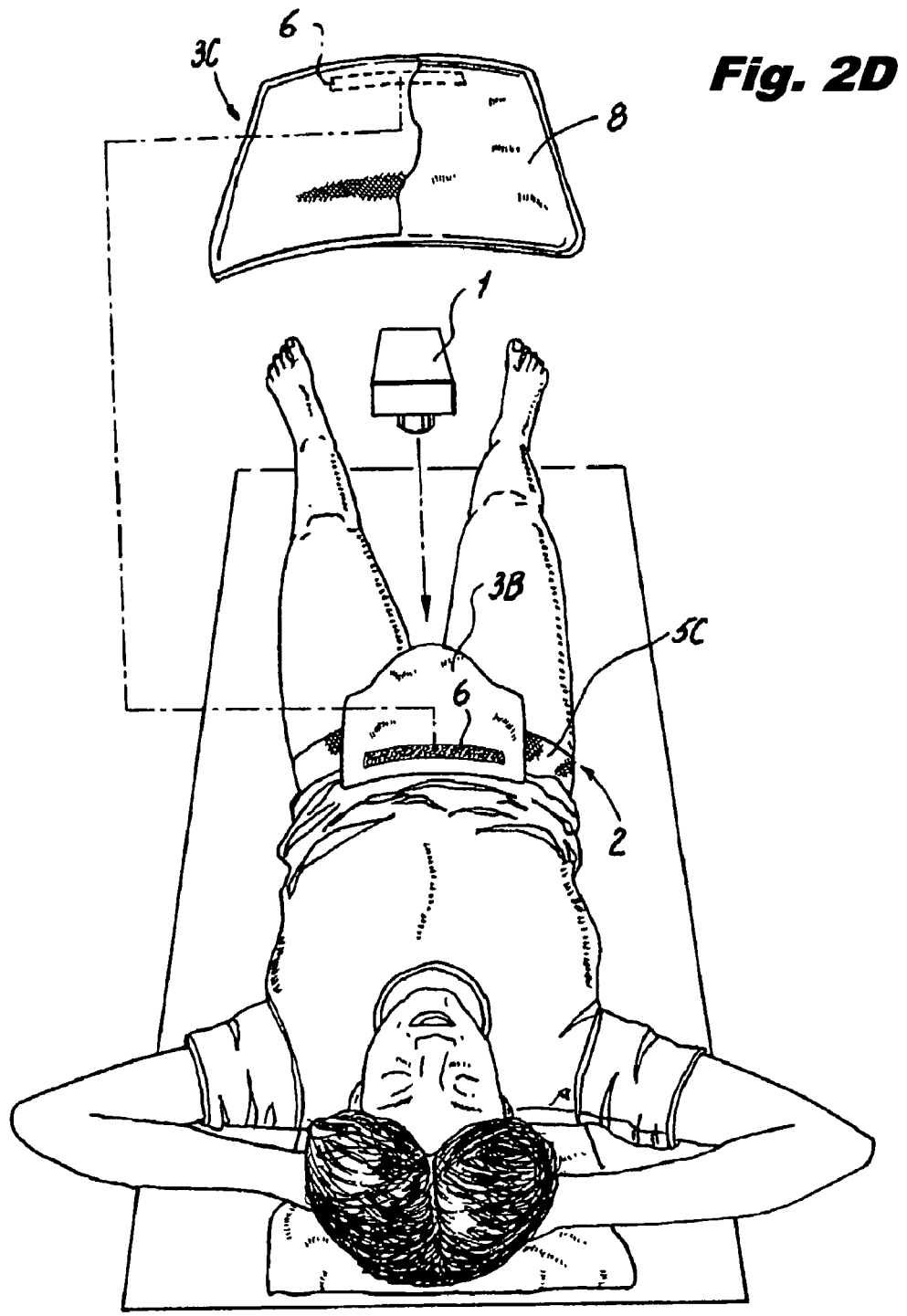

Referring now to FIG. 2D, target 2 is positioned below a users hips, spanning both hips. It is desirable in this circumstance to only image the external portions of the users hips while protecting the reproductive organs and the torso region. Here, while imaging both hips it is necessary to "window" both hip joints by securing a central shield 3B to a bikini 5C while simultaneously securing a third protective layer 3C to an external fixing portion 6 on bikini shield 3B. In this manner, the patient is well protected and the shielding is held securely in place by the user-containing bikini 5C which fixes both shields 3B, 3C is position. The resultant image allows the use of the required radiation and generates views of both hip joints with unduly exposing the patient's soft tissue to damage.

Figure 2E:
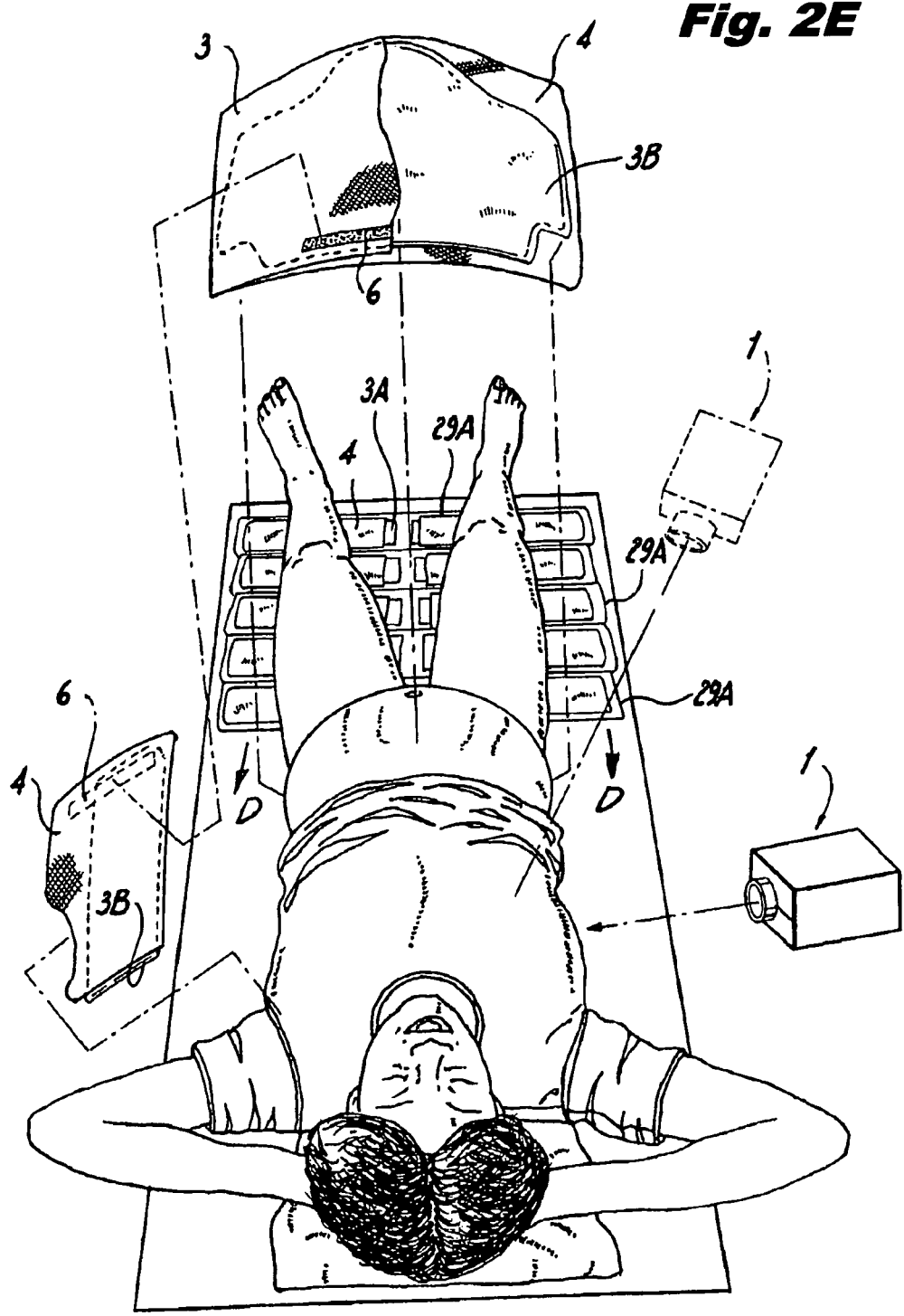
FIG. 2E is a perspective view of a shielding system according to another embodiment of the present invention for protecting a pregnant patient wherein front and side shields are self supportive for fetus protection and a bottom shield is provided to minimize reflected radiation.

Referring now to FIG. 2E where a more complex windowing assembly is provided according selected aspects of the present invention. As shown, it is desired to image a pregnant patient's right upper shoulder. While not shown, the user is wearing bikini system 5C below the curve of the projected belly. A curved removable shield 3 is formed from a pocket of material 4 having capacity slightly larger than prepared shielding member 3B. Pocket 4 in this situation is loose and contains bottom fixture location 6 (Velcro®) on a top (shown) and bottom underside (not shown) region. A separate pocket member 4 shaped as a shoulder guard member is similarly provided with a bottom underside fixture location 6 (shown) so as to fixably engage the top fixture location 6 on the belly pocket 4 to prevent slippage during patient movement. As shown shoulder guard pocket 4 contains a rectilinear shield member 3B so that from a front position, the patient is covered allowing a "window" for imaging the upper right shoulder.

Additionally, as will be discussed in greater detail, a bottom guard member formed from a single roll 29A is formed having a plurality of adjacent pockets 4 for receiving respective pluralities of shields 3A in an overlapping manner. As is noted, single roll shield 29A is drawing in direction D upwardly until reaching the shoulder region along the patient's dorsal side so as to minimize the impact of scattered radiation.

Figure 3A:
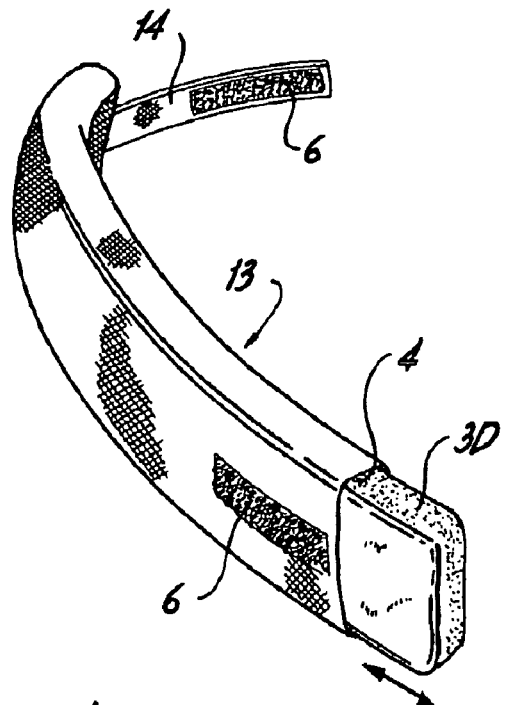
FIG. 3A is a perspective view of a shielding system for protecting a user's neck and thyroid region according to another embodiment of the present invention.

Referring now to FIG. 3A, a neck shield 13 is provided forming a pocket 4 having an elongated shape for receiving a segmented shielding member 3D retained in position about a user's neck via a strap 14 engaging respective securing Velcro members 6, 6, as shown. This embodiment responds to a need for protecting a use's thyroid and vocal region from high energy (X-ray or gamma ray) radiation.

Figure 3B:
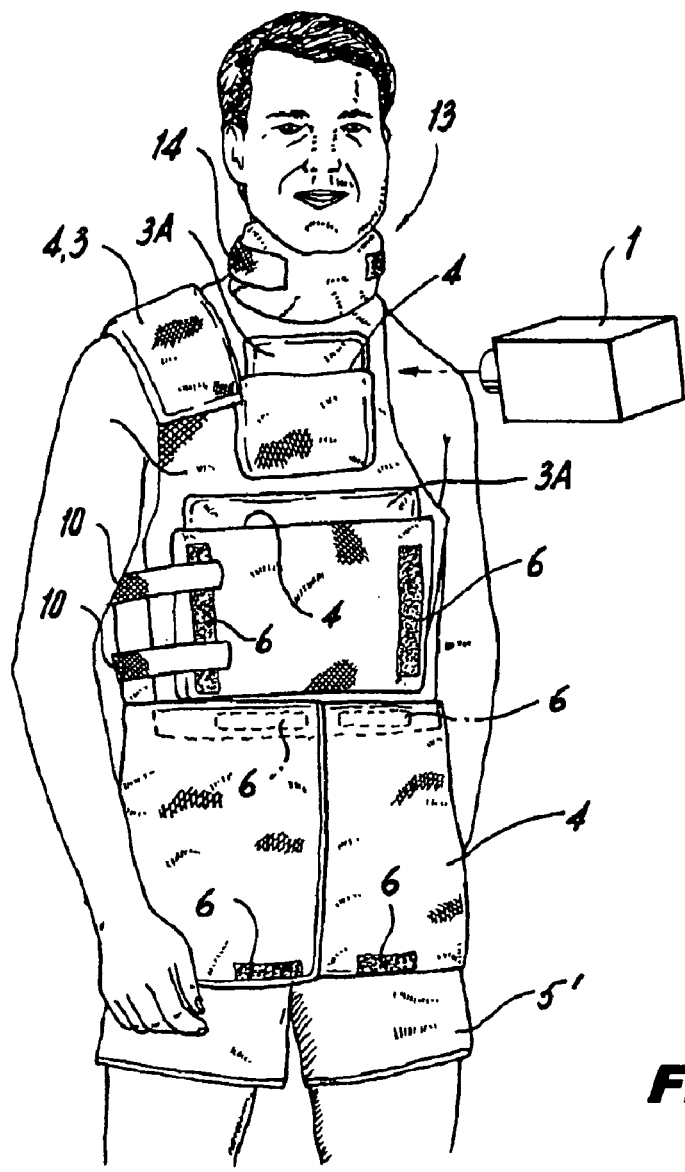
FIG. 3B is a perspective view of a user with multiple disposable protective shielding systems in place according to the present invention and preparing to image a left-shoulder region.

Additionally referring now to FIG. 3B, a vest assembly 15 is provided having a front and back region joined by shoulder straps bounding a neck opening, as shown. Side straps 10, 10 under each arm joint respective front and back regions to secure assembly 15 on the user as shown. Similarly a brief assembly 5' is worn by the user constructed in a manner similar to boxer-type shorts. A plurality of differently sized and positioned pockets 4 are located on vest assembly 15. In this circumstance it is desired to image the user's left shoulder and so pockets 4 are positioned along the right shoulder strap and the central chest region for receiving appropriately sized shielding layers 3, 3A. Also noted is that an external front bottom portion of vest assembly 15 is provided with attachment features 6 allowing the inclusion of skirt-shaped pockets 4 for added protection.

Figure 3C:
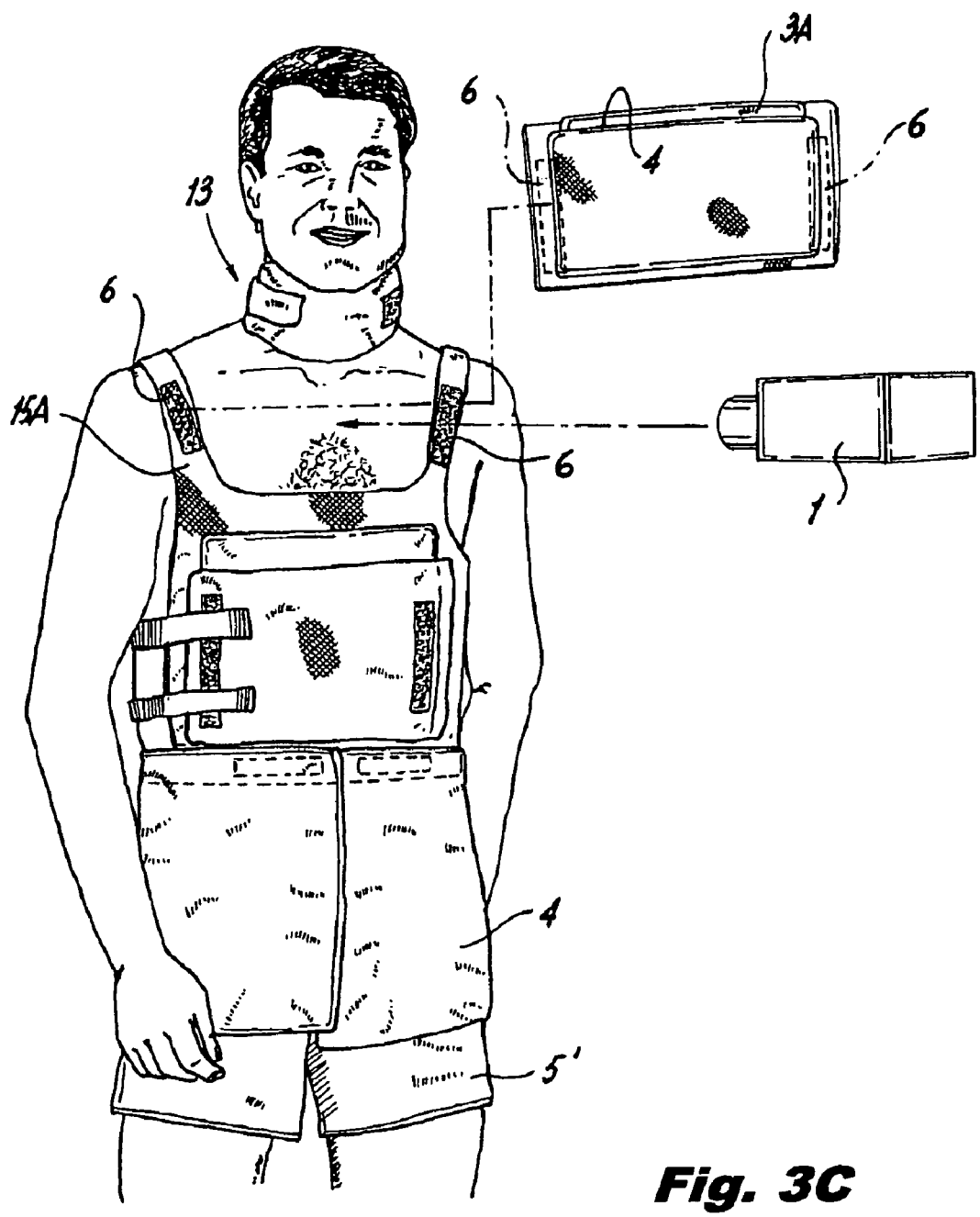
FIG. 3C is a perspective view of a user with multiple disposable protective shielding systems, including layering protection in place according to aspects of the present invention and preparing to image the central chest region.

Referring now to FIG. 3C an alternative vest construction system 15A is provided in a form having front and rear portions joined by shoulder straps as shown. While construction is similar to system 15 noted earlier, the detail noted here is the position of an external pocket 4 shaped to span between the shoulder straps and engage respective Velcro® regions 6 while retaining an appropriately sized shielding member 3A. As shown, the imaging goal here is the central upper chest of the user, and so neck member 13 is positioned and vest construction system 15A is adopted to provide an imaging window bounded generally protective shields retained in pockets or sleeves.

Figure 4A:
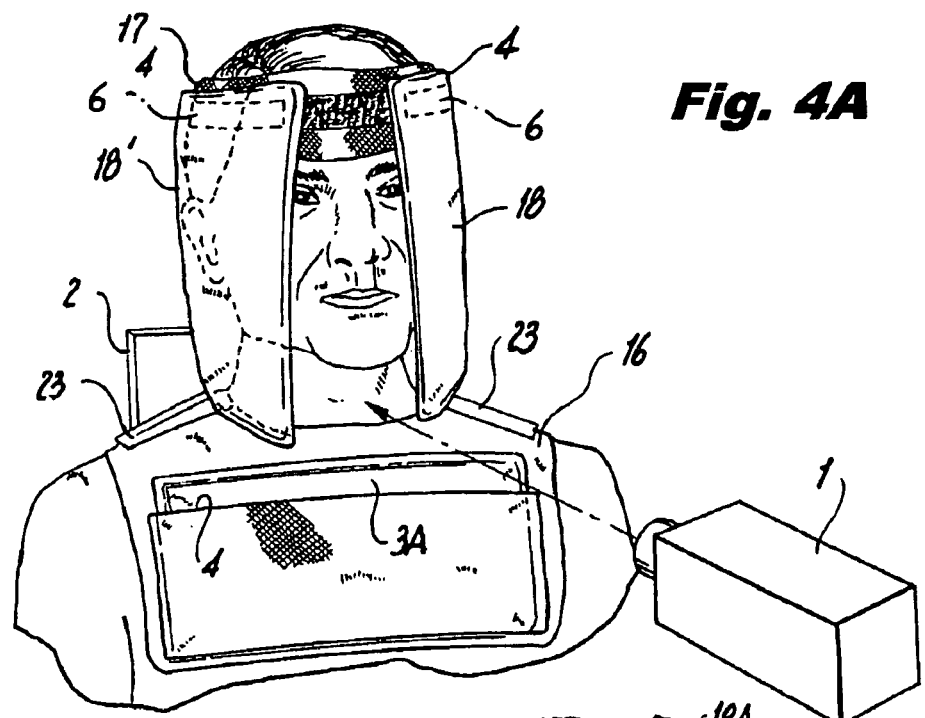
FIG. 4A is a perspective view of a user with multiple protective shielding systems in place, including a skull protective embodiment, prior to imaging a thyroid region. As noted, the shielding systems are effective to provide a "windowing-capable system" mechanism while allowing the user's imaging needs to succeed.

Referring now to FIG. 4A, an imaging goal is the central nasal and through region of a user. Here a dickey or upper shoulder system 16 is combined with a headband system 17 for supporting a plurality of shield members in a windowing manner as will be noted from the image.

Dickey system 16 includes a central front pocket member shown at 4 for containing a removable shield member 3A. Head band 17 includes a Velcro® outer portion (as shown) that engages and suspends left and right side partial-arc shields 18, 18' enclosed within respective pocket portions 4, 4. As will be appreciated from the present construction, arc shields are easily repositionable or overlap-able so as to section or "window" a portion of a user's head to minimize damaging radiation exposure. In the variant system shown, dickey system 16 includes shoulder joints 23, 23 that engage and retain partial-arc shield pockets for stability.

Figure 4B:
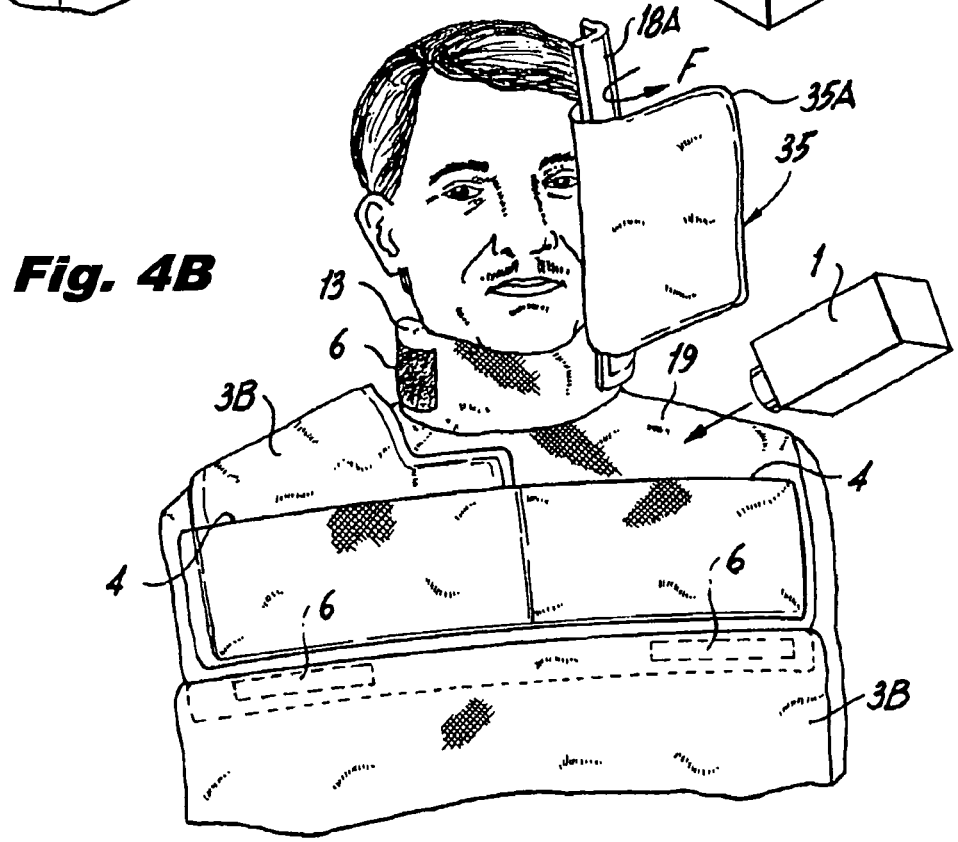
FIG. 4B is a perspective view of a user with an alternative multiple shielding system in place, using an alternative "windowing-capable" system allowing successful imaging while reducing patient exposure.

Referring now to FIG. 4B, an alternative system, referred hereinto as a half-poncho system 19 includes a plurality of pockets that enable imaging of a user's left shoulder. A series of appropriately shaped pockets 4 contain a flexible, wrap-around shield 3B. Used concurrently with neck shield 13 and a face-extension shield system 35 extending there from, the user's shoulder is "windowed" for imaging while minimizing user exposure.

As shown, face-extension shield system 35 consists of an extending semi-rigid member 18A fixed to an external Velcro® fixture portion 6, as shown. Shield system 35 also includes a flexible shield pocket member 35A (shown folded back at F) constructed as a pocket 4 containing a shield (not shown) and joined along rigid member 18A. During use, it will be appreciated by those of skill in the art, that shield system 35 may be folded back to cover the user's face to provide greater protection. Of course, following use, each shield member may be removed from their respective pockets 4 for cleaning and pocket materials and half-poncho system 19 may be simply discarded for cleanliness.

Figure 5A:
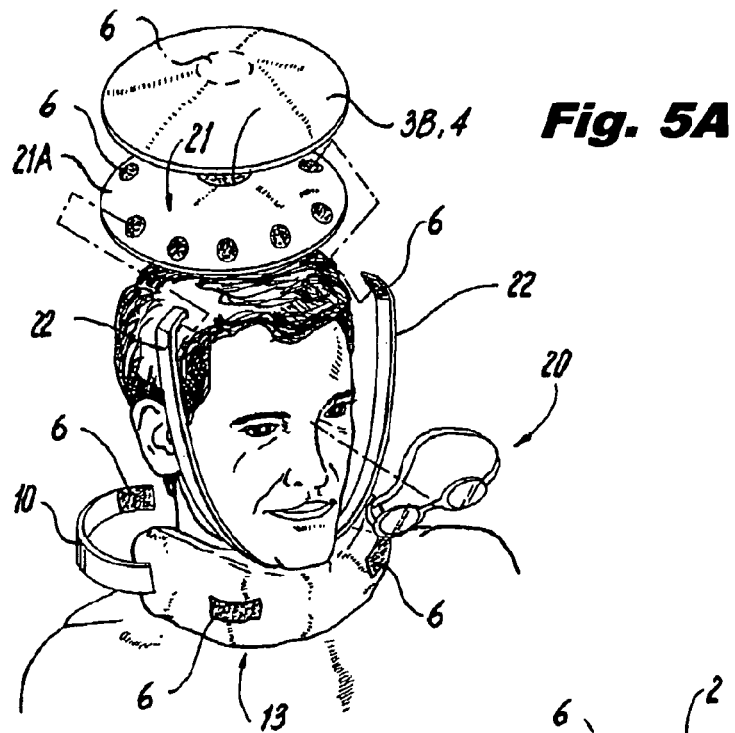
FIG. 5A is a perspective partially exploded view of a skull imaging assembly employing multiple aspects of the present invention to "window" a desired radiation region of a patient.
Figure 5B:
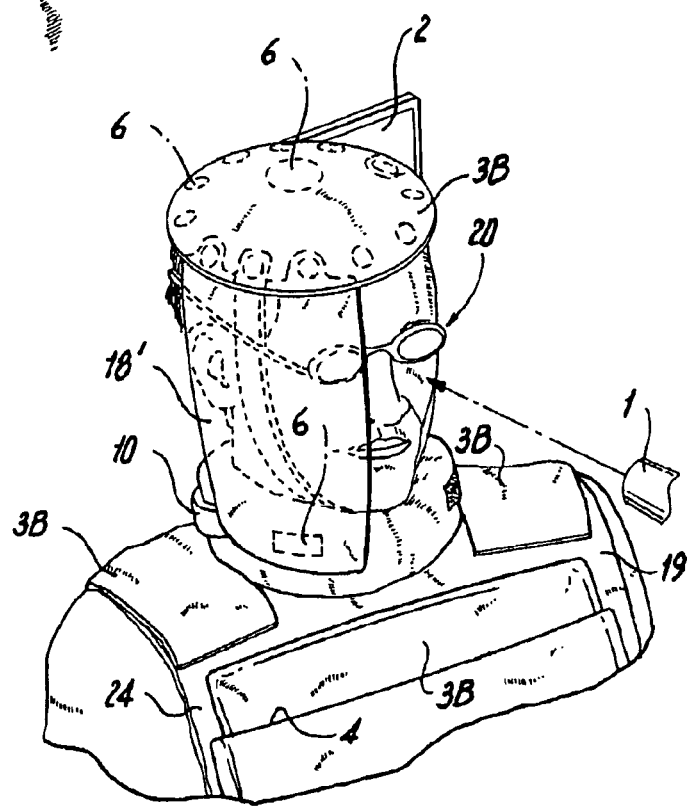
FIG. 5B is a perspective assembled view of a possible skull imaging assembly related to the depiction of FIG. 5A.

Referring now to FIGS. 5A and 5B, an adaptive skull protection system 21 is provided in combination with neck protective system 13. Here, it is desired to image a user's left facial side/ocular region, and accordingly, skull protection system includes a head support member 21A and a support strap 22 reaching between corresponding engaging regions 6. A head-top pocket 4 contains a shielding member 3B and is similarly joined to respective engaging regions 6 on head support member 21A. A side shield member 18', introduced earlier is similarly joined and spans between skull protection system 21 and neck member protection system 13, as shown. Semi-poncho system 19 is similarly provided with a plurality of overlapping shielding members 3B. Additionally provided are X-ray protective lead goggles 20 having a narrow profile for only protecting the user's eye ball (similar to sun-tanning-type goggles). In this manner it will be appreciated that combining protective shielding systems enables variable windowing options for imagery without departing from the scope and spirit of the present disclosure.

Figure 6A:
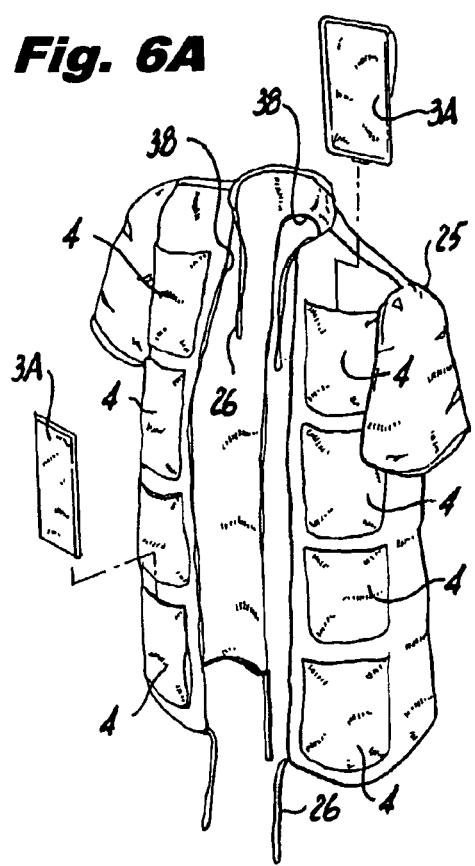
FIG. 6A is a perspective view of a vest-type system for spinal imagery with adaptable overlapping shielding plate members and window-capable construction.

Referring now to FIG. 6A, a coat type shielding system 25 is proposed having arm openings and arc-shaped body coverings bounding front and rear slits 38, 38 with top and bottom securing string members 26. Coat system 25 allows ready imaging and windowing of a user's spinal column while providing numerous pockets 4 for containing overlapping shielding members 3A.

As will be appreciated in this context, each shielding member 3A is longer in dimension then each respective pocket 4, so that when all pockets 4 are filled with shields 3A a continuous, yet flexible, shielding barrier extends on both sides of a user's spine. To employ shielding system 25, a user inserts arms through sleeve openings and secures strings 26, 26.

Figure 6C:
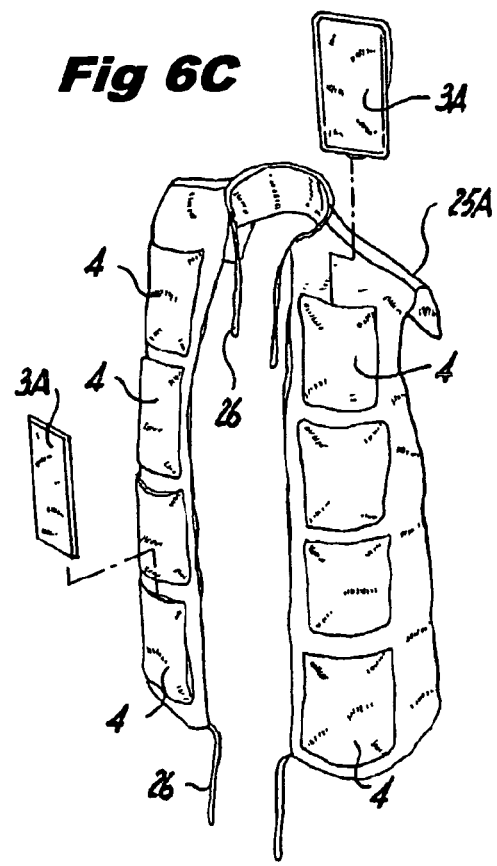
FIG. 6C is a perspective view of a shawl-type system for spinal imagery adapted for use with injured or disabled patients.
Figure 6D:
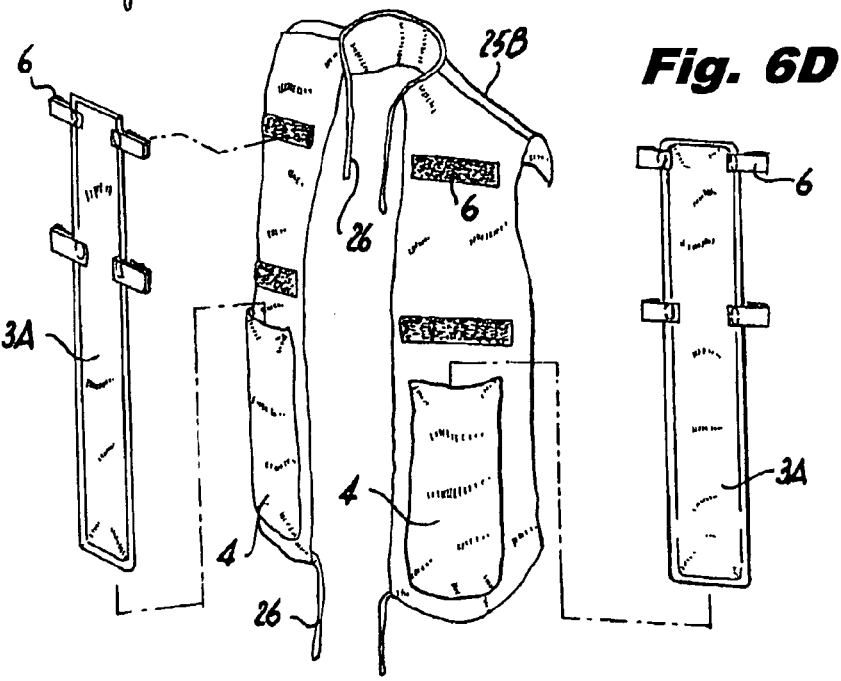
FIG. 6D is a perspective view of an alternative shawl-type system for spinal imagery with extended shield members.
Figure 6B:
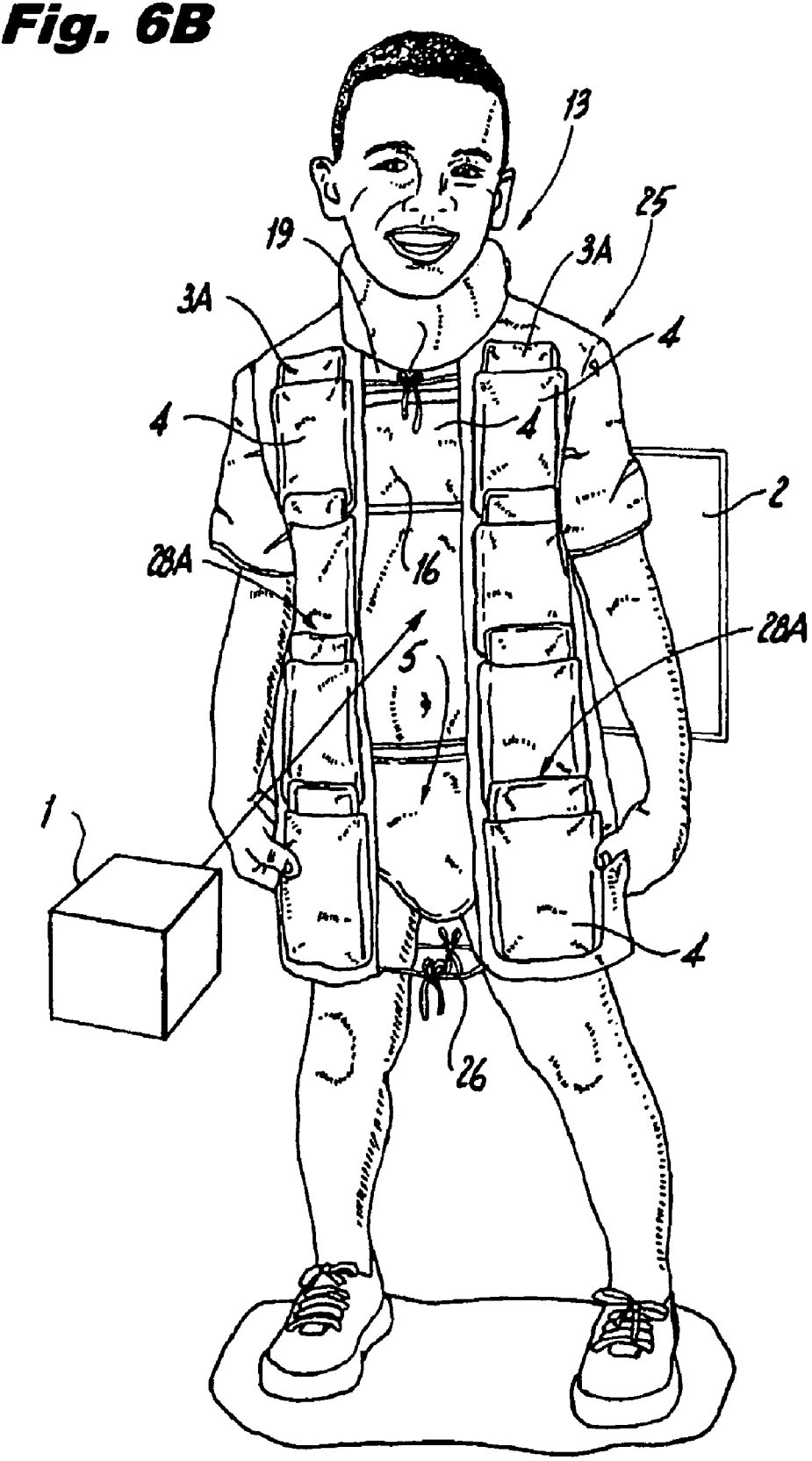
FIG. 6B is a perspective view of a user employing a vest-type system, as in FIG. 6A, for central spinal imagery with additional pelvic, thyroid, and upper-chest protection providing a window-capable arrangement for spinal viewing.

Referring now to FIG. 6B it will be appreciated that coat type shielding system 25 may be combined with other herein-described systems, including neck shielding system 13, brief shielding system 5, and semi or partial poncho system 19. In the view provided, the overlapping nature of shields 3A is clearly visible, and in combination with the other shielding systems employed provides a ready "windowing" of a user's central spinal region. Thus, it will be appreciated that combining aspects of the present short use system while convenient for cleaning and adaptive to emergency use, are also readily combinable to address a common medical imaging need. Similarly, this type of combination may be commonly prepared in a pre-staged kit form to address a repeated imaging need.

Referring now to FIG. 6C a front draping shield system 25A is formed similarly to coat type system 25, but provides only narrow front support panels for carrying pockets 4, as shown. This present draping shield system is proposed for those patients who may have physical difficulty when dealing with arm openings or who have a limited range of arm movement. Similarly, draping shield system 25A may be readily placed on a reclined patient for spinal imagery without having to move the patient.

Referring now to FIG. 6D, a variant of the above design is shown as front draping shield system 25B wherein pockets 4 are combined into one extended support pocket 4 for receiving an extended flexible shielding member 3A retain-able on Velcro® fastening regions 6. System 25B is proposed for specialized use where a medical office requires frequent spinal imagery and seeks to minimize the time repositioning shielding elements 3A.

Figures 7A, 7B:
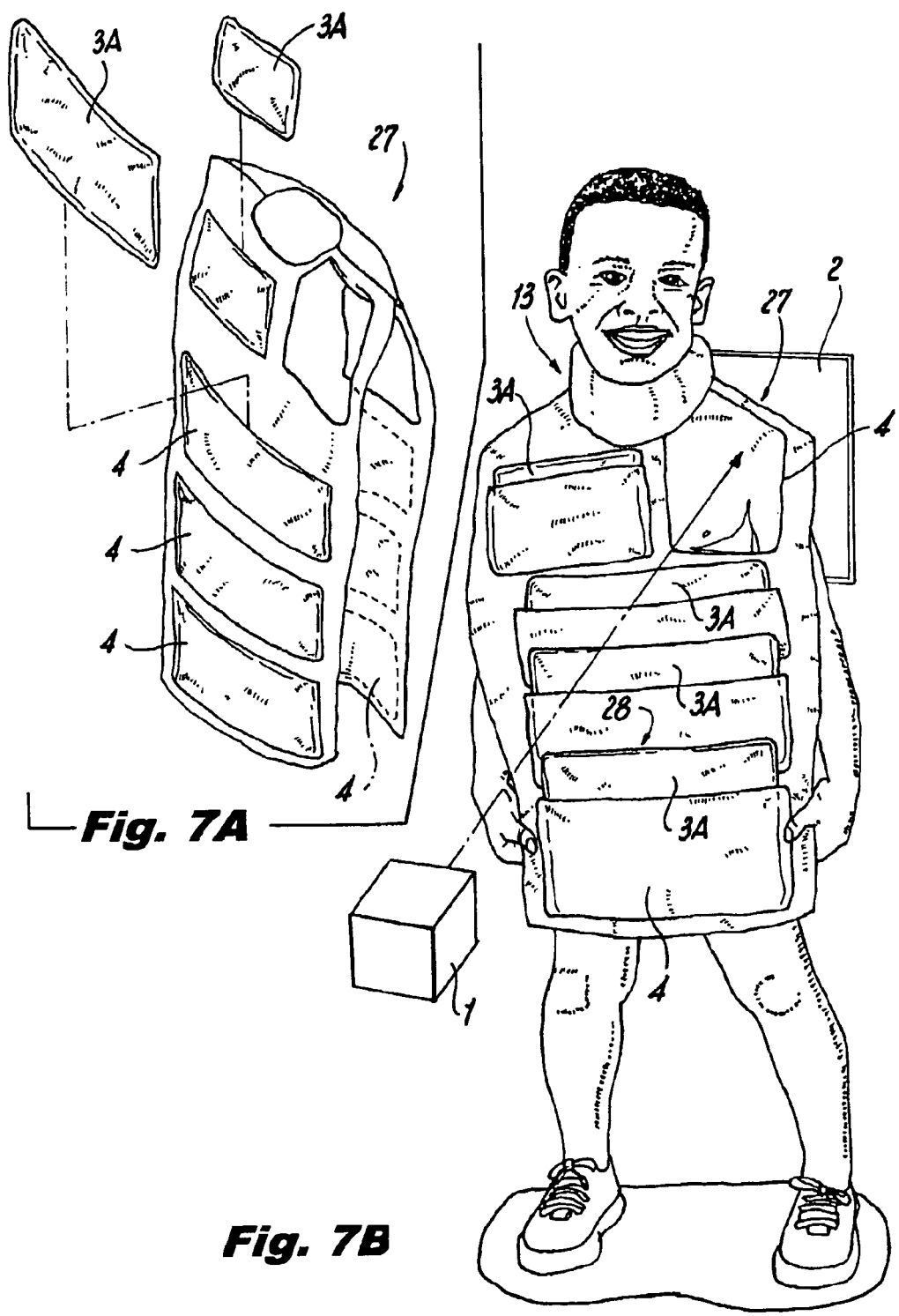
FIG. 7A is a perspective view of a poncho-type protective garment system.
FIG. 7B is a perspective view of a poncho-type system as in FIG. 7A employed with shielding and other system elements to protect a patient for left-shoulder imagery employing the window-capable function of the present system. It is noted that this poncho-type system may include pockets on both shoulders, and a radiation shield in only one so as to allow window-capable imagery.

Referring now FIGS. 7A and 7B a full-poncho shielding system 27 is provided having a complete front and back portion joined by shoulder regions, as shown. A plurality of pockets 4 are positioned on both front and back regions and allow for overlapping of shielding members 3A. An overlapping portion 28 is noted specifically in FIG. 7B. It will be appreciated that for select individuals, for example those requiring wheel chair assistance and support, full-poncho system 27 provides a substantial advantage.

As noted in FIG. 7B, a patient's left shoulder region is exposed for imagery within a window by removing (or not inserting) a left-shoulder shield 3A and installing a neck shielding system 13. Those appreciating the disclosure herein will similarly recognize the capacity to "window" other regions of the user by repositioning shield members 3A.

Figures 8A, 8B:
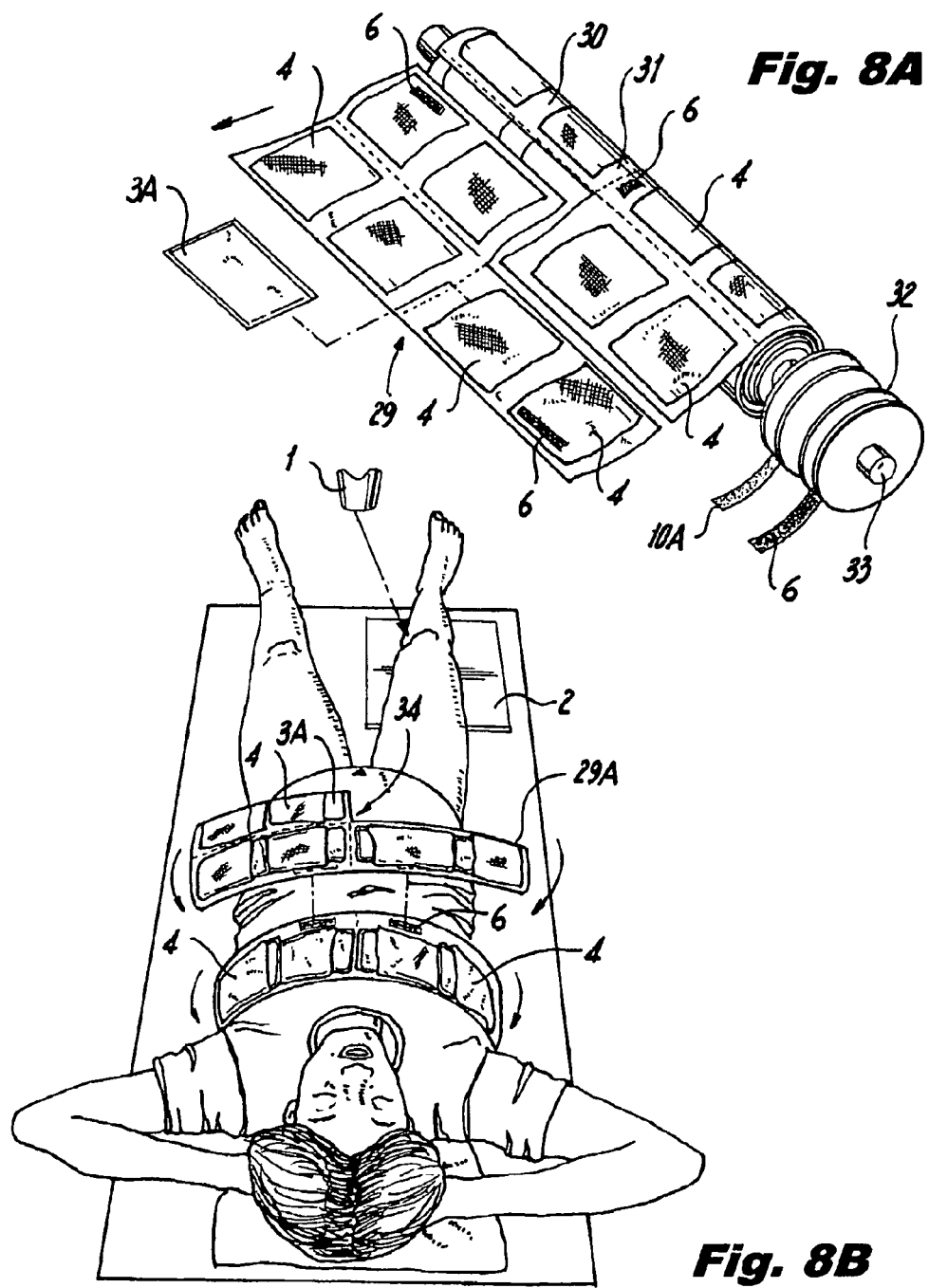
FIG. 8A is a perspective view of an adaptive protective garment system noting a roll of attachment points or pockets, and spare attachment items such as Velcro®, wherein the disposable or single use protective garment roll includes a plurality of preferred failure locations as stress-concentrators or removal-enhancers for preferred tearing-off to suit a particular window-capable use.
FIG. 8B is a perspective view of a user prior to imaging with the adaptive garment system of FIG. 8A positioned to minimize undesirable exposure for a patient that is immobile.

Referring now to FIG. 8A, an adaptive shielding system 29 is provided in the form of a continuous tear-off-type roll or sheet stock pivotable about an axis 33. Shielding system 29 is provided with a series of perforations 31 interposed with respective pockets 4 and open regions 30 covered by overlapping portions 28 of shield members 28 when in use. A plurality of attachment points 6 are distributed on pockets 4 and on sheet material open regions 30 so as to allow ready positioning prior to use. System 29 may be optionally provided with rolls 32 of variously selected engagement members such as Velcro® straps 6 or adhesive backed straps 10A.

As will be appreciated by those of skill in the art, system 29 allows ready deconstruction in to sub-parts or shapes for covering a disabled or injured patient while still carrying shielding members 3A in one or more pockets 4, each securable by respective attachment portions 6 (for example Velcro strips). Thus, where a medical need exists to cover a distended abdomen, a user may simply measure out a required length of sheet 30 and cut it to length, insert multiple shields and cover the patient with a disposable or short-use radiation shield. In this way, those of skill in the art will recognize that shielding system 29 allows ready operation as an emergency room kit adaptable to constantly changing circumstances.

Referring now to FIG. 8B, a patient is positioned having a distended abdomen and therefore being unable to fit within many of the standard briefs or bikini systems noted earlier. As a consequence, a user may adapt the sheeting system shown in FIG. 8A to a patient condition for protection, and simply dispose of the sheet good after use, retaining the shielding members 3A for later reuse.

Figure 9A:
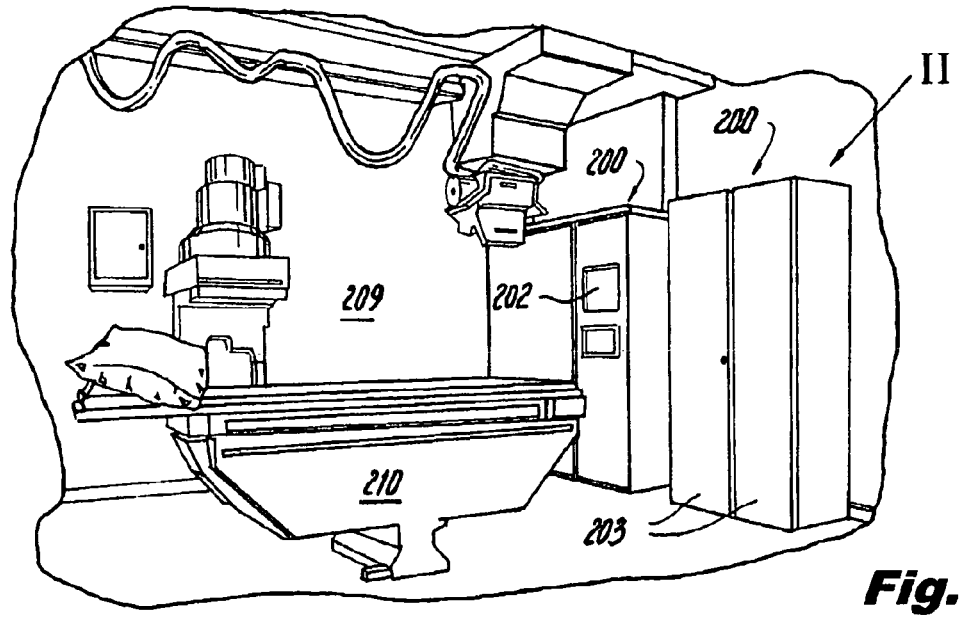
FIG. 9A is a perspective view of a medical imaging center containing a comprehensive storage kit of adaptive short-use protective systems according to the present invention.
Figure 9B:
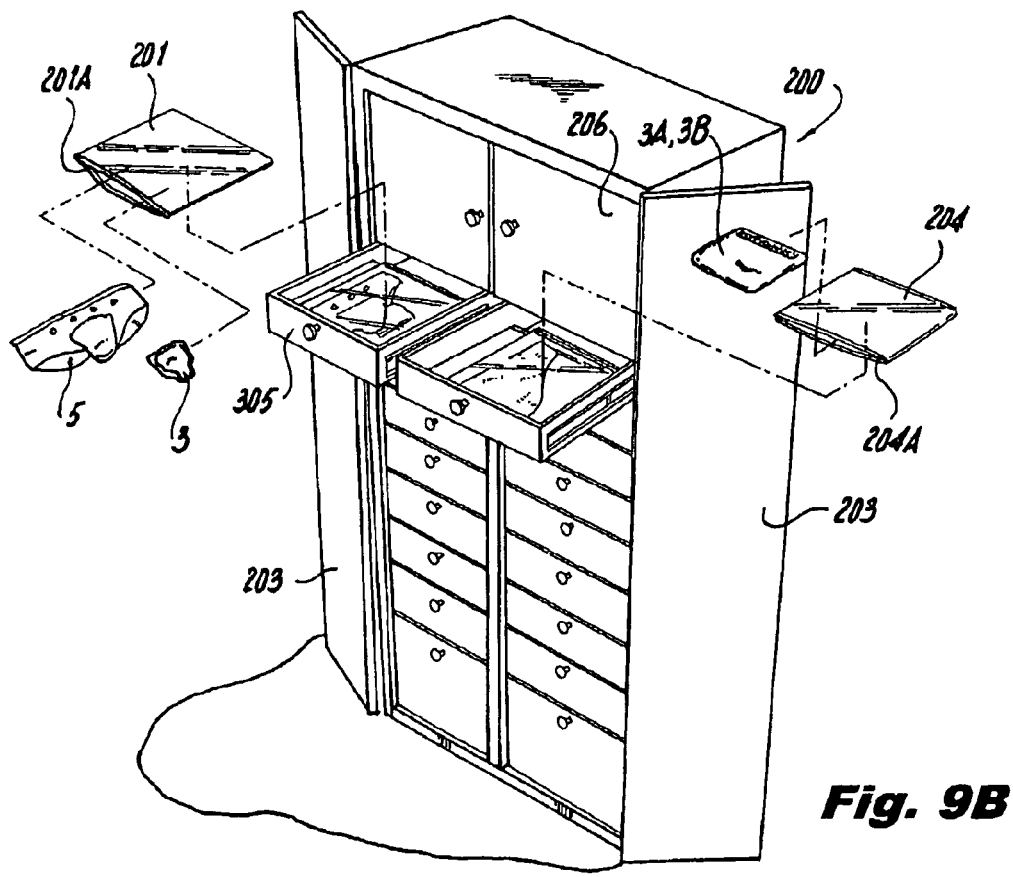
FIG. 9B is a perspective exploded view of a storage kit for multiple ready-to-use protective systems according to the present invention.

Referring now to FIGS. 9A and 9B, a comprehensive short use assembly system 200 is provided within cabinets having doors 203, 203 that may be readily positioned within an imaging room 201 proximate an imaging unit 210 for convenient access. An order center 202 may be provided on the cabinet system and contain convenient web-based, or form-based reordering and an identifiable listing of items so that restocking of drawers 305 with respective prepackaged sealed kits 204 is easily achieved. Sealed kits 204 contain shielding units 3A, 3B while complete system sealed kits 201 may contain both a shielding system (here brief shielding system 5) with a shielding member 3. In either circumstance sealed kits 204, 201 are ready use pre-packaged kits stored and labeled according to a responsive need and may be stored in drawers 305 or for larger kits, within larger doors 206. For example, in an emergency room an large abdominal shield for pregnant patients may be stored behind doors 206 while the flexible pocket 4 shaped to contain such a shield may be stored in a sealed and sterilized packet 201.

As used herein, the phrase disposable or disposable member layer etc. is intended to be interpreted broadly and without limitation to be an item that is not intended for long-term re-use. Thus, for example while a preferred embodiment may provide a single-use disposable member constructed from a Tyvek®-like or a thin-film polymer baby-diaper-like material, a woven sheet good such as inexpensive cotton or nylon weave, or a natural fiber based good such as paper, nothing herein shall be interpreted to restrict the phrase disposable to such goods. As a second example, where a user provides the member layers from a more traditional cloth or more expensive or multiple-use-capable material, the present invention envisions these items as also being "disposable" within the present scope as each one may be employed without an intention to reuse. Similarly, the phrase disposable as used herein shall not mandate single use prior to disposal, where for example a child is equipped with a brief as in FIG. 1A for an initial imagery use, this may be removed for surgical treatment, and reused for after-treatment imagery without departing from the scope and meaning of the present invention because the garment is intended for ultimate disposal.

As those of skill in the art will recognize, the present invention introduces a protective imaging system that is fully capable of "windowing" a desired image region, or in other words the present system is capable of multiple adaptations that allow substantive shielding of non-target body regions while allowing a narrowly defined radiation entry path for imaging a target body region. This concept of "windowing" is applicable to all areas of a user's body so as to minimize a user's radiation exposure to non-target regions and therefore enhance patient safety.

Finally, those of skill in the art of adaptive fastening will recognize that while the present discussion may identify fixed snap point, a double tab overlap, a pocket, a magnet member, a Velcro® patch, a buckle, or a tab member for example, nothing is intended herein to restrict the discussion to these forms of attachment mechanisms to those examples identified. It is intended that the phrase "attachment mechanism" or attachment means or means for attachment shall be inclusive each of these types of attachment systems and shall similarly incorporate other forms of attachment mechanisms and systems known to the art.

In the claims, means- or step-plus-function clauses are intended to cover the structures described or suggested herein as performing the recited function and not only structural equivalents but also equivalent structures. Thus, for example, although a nail, a screw, and a bolt may not be structural equivalents in that a nail relies on friction between a wooden part and a cylindrical surface, a screw's helical surface positively engages the wooden part, and a bolt's head and nut compress opposite sides of a wooden part, in the environment of fastening wooden parts, a nail, a screw, and a bolt may be readily understood by those skilled in the art as equivalent structures.

Having described at least one of the preferred embodiments of the present invention with reference to the accompanying drawings, it is to be understood that the invention is not limited to those precise embodiments, and that various changes, modifications, and adaptations may be effected therein by one skilled in the art without departing from the scope or spirit of the invention as defined in the appended claims.

What is claimed is:

1. A garment for use during procedures that expose a portion of a user to high energy radiation from a radiation source, comprising:
   a disposable short-use flexible garment member;
   said disposable short-use flexible garment member having an opening for encircling the user's waist and having two openings for receiving the user's legs;
   a means for removably securing said disposable short-use flexible garment member on said user prior to receiving said high energy radiation;
   a first pocket defining member located on an outer surface of said disposable short-use flexible garment member for removably receiving a first flexible shielding member there within
   said disposable short-use flexible garment member extending beyond a side edge of said first pocket defining member;
   at least one attachment portion located on the outer surface of said disposable short-use flexible garment member for attaching a second flexible shielding member, wherein the attachment portion is positioned relative to the first pocket defining member such that when the second flexible shielding member is attached via the attachment portion it partially overlaps the first flexible shielding member within the first pocket defining member.

2. A garment, according to claim 1, wherein:
   the at least one attachment portion for attaching said second flexible shielding member is a second pocket defining member.

3. A garment, according to claim 1, wherein:
   said means for securing said disposable short-use flexible garment member on said user further comprises, at least one means for releasably securing said disposable short-use flexible garment member on said user selected from the group comprising:
   an adhesive member, a mechanical securing member, a magnetic member, a string-tie member, a strap member, a mechanical snap member, a hook-and-loop based mechanical fastener member; and an elastic member.

4. A garment, according to claim 1, wherein:
   the at least one attachment portion includes at least one of a removable pocket defining member, a pocket defining member immovably fixed to said disposable short-use flexible garment member, a hook-and-loop based mechanical fastener system, a mechanical snap member, a string-tie member, a strap member, and an adhesive member.

5. A garment, according to claim 1, wherein:
   said disposable short-use flexible garment member is constructed from at least one of a woven layer material and a non-woven layer material.

6. A garment, according to claim 5, wherein:
   said disposable short-use flexible garment member is constructed from said non-woven layer material; and
   said non-woven layer material is one of an inelastic material and an elastic material.

7. A garment, according to claim 1, further comprising:
   a plurality of additional pocket defining members located on an outer surface of said disposable short-use flexible garment member defining a respective plurality of pocket locations for removably receiving a respective plurality of flexible shielding members there-within during a use thereof.

8. A garment, according to claim 1, wherein:
   said first pocket defining member extends from the top of the garment down to between the garment's leg openings on the front side of the user's body.

9. A garment according to claim 8, further comprising an additional pocket defining member from the top of the garment down to between the garment's leg openings on the rear side of the user's body.

10. A garment according to claim 1, wherein said means for securing said disposable short-use flexible garment member on said user further comprises an elastic waist member for securing the garment around the user's waist.

11. A garment for use during procedures that expose a portion of a user to high energy radiation from a radiation source, comprising:
    a disposable short-use flexible garment member;
    said disposable short-use flexible garment member having a length greater than a width, wherein the width is between about 2 inches to about 5 inches;
    a means for removably securing the garment around a user's neck wherein the length of the garment member encircles the user's neck;
    a means for removably securing said disposable short-use flexible garment member around the user's neck prior to receiving said high energy radiation
    a pocket defining member on said disposable short-use flexible garment member for removably receiving a flexible shielding member therewithin;
    a means for removably securing a second flexible shielding member to the outer surface of said short-use flexible garment member, wherein said second flexible shielding member is positionable such that it overlaps said first shielding member.

12. A garment for use during procedures that expose a portion of a user to high energy radiation from a radiation source, comprising:
    a generally rectangular disposable short-use flexible garment member having a front panel and a back panel;
    said disposable short-use flexible garment member further comprising a means for removably securing said disposable short-use flexible garment member on said user prior to receiving said high energy radiation wherein the front panel lays against the user's front and the back panel lays against the user's back;

said means for removably securing the garment on the user includes at least one of an adhesive member, a mechanical securing member, a magnetic member, a string-tie member, a strap member, a mechanical snap member, a hook-and-loop based mechanical fastener member; and an elastic member;

a pocket defining member located on an outer surface of the front panel of said disposable short-use flexible garment member for removably receiving a first flexible shielding member there within; and a means for removably securing a second flexible shielding member to an external region of the front panel of said disposable short-use flexible garment member, wherein said second flexible shielding member is positionable such that it overlaps a portion of said first flexible shielding member.

13. A garment, according to claim 12, wherein said means for removably securing a second flexible shielding member includes at least one of a removable pocket defining member, a pocket defining member immovably fixed to said disposable short-use flexible garment member, a hook-and-loop based mechanical fastener system, a mechanical snap member, a string-tie member, a strap member, and an adhesive member.

14. A garment for use during procedures that expose a portion of a user to high energy radiation from a radiation source, comprising:

a generally rectangular disposable short-use flexible garment member having a front panel and a back panel;

said disposable short-use flexible garment member further comprising a means for removably securing said disposable short-use flexible garment member on said user prior to receiving said high energy radiation, wherein the front panel lays against the user's front and the back panel lays against the user's back;

said means for removably securing the garment on the user includes at least one of an adhesive member, a mechanical securing member, a magnetic member, a string-tie member, a strap member, a mechanical snap member, a hook-and-loop based mechanical fastener member; and an elastic member;

a first pocket defining member located on an outer surface of the front panel of said disposable short-use flexible garment member for removably receiving a first flexible shielding member there within; and a second pocket defining member for removably receiving a second flexible shielding member, wherein the second pocket defining member is positioned relative to the first pocket defining member such that when the second flexible shielding member is placed in the second pocket defining member it partially overlaps the first flexible shielding member when placed in the first pocket defining member.

* * * * *